(12) United States Patent
Smith et al.

(10) Patent No.: US 9,192,355 B2
(45) Date of Patent: Nov. 24, 2015

(54) MULTIPLE APERTURE ULTRASOUND ARRAY ALIGNMENT FIXTURE

(71) Applicant: Maui Imaging, Inc., Sunnyvale, CA (US)

(72) Inventors: David M. Smith, Lodi, CA (US); Sharon L. Adam, San Jose, CA (US); Donald F. Specht, Los Altos, CA (US); Kenneth D. Brewer, Santa Clara, CA (US); John P. Lunsford, San Carlos, CA (US)

(73) Assignee: MAUI IMAGING, INC., Sunnyvale, CA (US)

( * ) Notice: Subject to any disclaimer, the term of this patent is extended or adjusted under 35 U.S.C. 154(b) by 242 days.

(21) Appl. No.: 13/894,192

(22) Filed: May 14, 2013

(65) Prior Publication Data
US 2013/0247350 A1    Sep. 26, 2013

Related U.S. Application Data

(63) Continuation of application No. 12/760,327, filed on Apr. 14, 2010, now Pat. No. 8,473,239.

(60) Provisional application No. 61/169,200, filed on Apr. 14, 2009.

(51) Int. Cl.
*A61B 8/00* (2006.01)
*G01S 7/52* (2006.01)
(Continued)

(52) U.S. Cl.
CPC ... *A61B 8/42* (2013.01); *A61B 8/00* (2013.01); *A61B 8/4218* (2013.01); *A61B 8/587* (2013.01);
(Continued)

(58) Field of Classification Search
USPC .......................................................... 702/100
See application file for complete search history.

(56) References Cited

U.S. PATENT DOCUMENTS

| 3,174,286 A | 3/1965 | Erickson |
| 3,895,381 A | 7/1975 | Kock |

(Continued)

FOREIGN PATENT DOCUMENTS

| CN | 102123668 | 7/2011 |
| EP | 1949856 A1 | 7/2008 |

(Continued)

OTHER PUBLICATIONS

Belevich et al.; U.S. Appl. No. 13/964,701 entitled "Calibration of Multiple Aperture Ultrasound Probes," filed Aug. 12, 2013.

(Continued)

*Primary Examiner* — Tung S Lau
(74) *Attorney, Agent, or Firm* — Shay Glenn LLP

(57) ABSTRACT

Increasing the effective aperture of an ultrasound imaging probe by including more than one probe head and using the elements of all of the probes to render an image can greatly improve the lateral resolution of the generated image. In order to render an image, the relative positions of all of the elements must be known precisely. A calibration fixture is described in which the probe assembly to be calibrated is placed above a test block and transmits ultrasonic pulses through the test block to an ultrasonic sensor. As the ultrasonic pulses are transmitted though some or all of the elements in the probe to be tested, the differential transit times of arrival of the waveform are measured precisely. From these measurements the relative positions of the probe elements can be computed and the probe can be aligned.

14 Claims, 31 Drawing Sheets

(51) Int. Cl.
  *G01S 15/89* (2006.01)
  *A61B 8/08* (2006.01)

(52) U.S. Cl.
  CPC ........... *G01S 7/5205* (2013.01); *G01S 15/8913* (2013.01); *A61B 8/0883* (2013.01); *Y10T 29/49778* (2015.01)

(56) References Cited

U.S. PATENT DOCUMENTS

| | | |
|---|---|---|
| 4,055,988 A * | 11/1977 | Dutton, Jr. .................... 73/620 |
| 4,072,922 A | 2/1978 | Taner et al. |
| 4,097,835 A | 6/1978 | Green |
| 4,105,018 A | 8/1978 | Greenleaf et al. |
| 4,259,733 A | 3/1981 | Taner et al. |
| 4,271,842 A | 6/1981 | Specht et al. |
| 4,325,257 A | 4/1982 | Kino et al. |
| 4,333,474 A | 6/1982 | Nigam |
| 4,339,952 A | 7/1982 | Foster |
| 4,452,084 A | 6/1984 | Taenzer |
| 4,501,279 A | 2/1985 | Seo |
| 4,539,847 A | 9/1985 | Paap |
| 4,566,459 A | 1/1986 | Umemura et al. |
| 4,567,768 A | 2/1986 | Satoh et al. |
| 4,662,222 A | 5/1987 | Johnson |
| 4,669,482 A | 6/1987 | Ophir |
| 4,682,497 A | 7/1987 | Sasaki |
| 4,781,199 A | 11/1988 | Hirama et al. |
| 4,817,434 A | 4/1989 | Anderson |
| 4,831,601 A | 5/1989 | Breimesser et al. |
| 4,893,284 A | 1/1990 | Magrane |
| 4,893,628 A | 1/1990 | Angelsen |
| 5,050,588 A | 9/1991 | Grey et al. |
| 5,141,738 A | 8/1992 | Rasor et al. |
| 5,161,536 A | 11/1992 | Vilkomerson et al. |
| 5,197,475 A | 3/1993 | Antich et al. |
| 5,226,019 A | 7/1993 | Bahorich |
| 5,230,339 A | 7/1993 | Charlebois |
| 5,269,309 A | 12/1993 | Fort et al. |
| 5,278,757 A | 1/1994 | Hoctor et al. |
| 5,293,871 A | 3/1994 | Reinstein et al. |
| 5,299,576 A | 4/1994 | Shiba |
| 5,301,674 A | 4/1994 | Erikson et al. |
| 5,305,756 A | 4/1994 | Entrekin et al. |
| 5,339,282 A | 8/1994 | Kuhn et al. |
| 5,340,510 A | 8/1994 | Bowen |
| 5,345,426 A | 9/1994 | Lipschutz |
| 5,355,888 A | 10/1994 | Kendall |
| 5,398,216 A | 3/1995 | Hall et al. |
| 5,409,010 A | 4/1995 | Beach et al. |
| 5,442,462 A | 8/1995 | Guissin |
| 5,503,152 A | 4/1996 | Oakley et al. |
| 5,515,853 A | 5/1996 | Smith et al. |
| 5,515,856 A | 5/1996 | Olstad et al. |
| 5,522,393 A | 6/1996 | Phillips et al. |
| 5,526,815 A | 6/1996 | Granz et al. |
| 5,544,659 A | 8/1996 | Banjanin |
| 5,558,092 A | 9/1996 | Unger et al. |
| 5,564,423 A | 10/1996 | Mele et al. |
| 5,568,812 A | 10/1996 | Murashita et al. |
| 5,570,691 A | 11/1996 | Wright et al. |
| 5,581,517 A | 12/1996 | Gee et al. |
| 5,625,149 A | 4/1997 | Gururaja et al. |
| 5,628,320 A | 5/1997 | Teo |
| 5,673,697 A | 10/1997 | Bryan et al. |
| 5,675,550 A | 10/1997 | Ekhaus |
| 5,720,291 A | 2/1998 | Schwartz |
| 5,720,708 A | 2/1998 | Lu et al. |
| 5,744,898 A | 4/1998 | Smith et al. |
| 5,769,079 A | 6/1998 | Hossack |
| 5,784,334 A | 7/1998 | Sena et al. |
| 5,785,654 A | 7/1998 | Iinuma et al. |
| 5,795,297 A | 8/1998 | Daigle |
| 5,797,845 A | 8/1998 | Barabash et al. |
| 5,798,459 A | 8/1998 | Ohba et al. |
| 5,820,561 A | 10/1998 | Olstad et al. |
| 5,838,564 A | 11/1998 | Bahorich et al. |
| 5,850,622 A | 12/1998 | Vassiliou et al. |
| 5,862,100 A | 1/1999 | VerWest |
| 5,870,691 A | 2/1999 | Partyka et al. |
| 5,876,342 A | 3/1999 | Chen et al. |
| 5,891,038 A | 4/1999 | Seyed-Bolorforosh et al. |
| 5,892,732 A | 4/1999 | Gersztenkorn |
| 5,916,169 A | 6/1999 | Hanafy et al. |
| 5,919,139 A | 7/1999 | Lin |
| 5,920,285 A | 7/1999 | Benjamin |
| 5,930,730 A | 7/1999 | Marfurt et al. |
| 5,940,778 A | 8/1999 | Marfurt et al. |
| 5,964,707 A | 10/1999 | Fenster et al. |
| 5,969,661 A | 10/1999 | Benjamin |
| 5,999,836 A | 12/1999 | Nelson et al. |
| 6,007,499 A | 12/1999 | Martin et al. |
| 6,013,032 A | 1/2000 | Savord |
| 6,014,473 A | 1/2000 | Hossack et al. |
| 6,048,315 A | 4/2000 | Chiao et al. |
| 6,049,509 A | 4/2000 | Sonneland et al. |
| 6,050,943 A | 4/2000 | Slayton et al. |
| 6,056,693 A | 5/2000 | Haider |
| 6,058,074 A | 5/2000 | Swan et al. |
| 6,077,224 A | 6/2000 | Lang et al. |
| 6,092,026 A | 7/2000 | Bahorich et al. |
| 6,122,538 A | 9/2000 | Sliwa, Jr. et al. |
| 6,123,670 A | 9/2000 | Mo |
| 6,129,672 A | 10/2000 | Seward et al. |
| 6,135,960 A | 10/2000 | Holmberg |
| 6,138,075 A | 10/2000 | Yost |
| 6,148,095 A | 11/2000 | Prause et al. |
| 6,162,175 A | 12/2000 | Marian, Jr. et al. |
| 6,166,384 A | 12/2000 | Dentinger et al. |
| 6,166,853 A | 12/2000 | Sapia et al. |
| 6,193,665 B1 | 2/2001 | Hall et al. |
| 6,196,739 B1 | 3/2001 | Silverbrook |
| 6,200,266 B1 | 3/2001 | Shokrollahi et al. |
| 6,210,335 B1 | 4/2001 | Miller |
| 6,213,958 B1 | 4/2001 | Winder |
| 6,221,019 B1 | 4/2001 | Kantorovich |
| 6,231,511 B1 | 5/2001 | Bae |
| 6,238,342 B1 | 5/2001 | Feleppa et al. |
| 6,246,901 B1 | 6/2001 | Benaron |
| 6,251,073 B1 | 6/2001 | Imran et al. |
| 6,264,609 B1 | 7/2001 | Herrington et al. |
| 6,266,551 B1 | 7/2001 | Osadchy et al. |
| 6,278,949 B1 | 8/2001 | Alam |
| 6,289,230 B1 | 9/2001 | Chaiken et al. |
| 6,304,684 B1 | 10/2001 | Niczyporuk et al. |
| 6,309,356 B1 | 10/2001 | Ustuner et al. |
| 6,324,453 B1 | 11/2001 | Breed et al. |
| 6,345,539 B1 | 2/2002 | Rawes et al. |
| 6,361,500 B1 | 3/2002 | Masters |
| 6,363,033 B1 | 3/2002 | Cole et al. |
| 6,374,185 B1 | 4/2002 | Taner et al. |
| 6,394,955 B1 | 5/2002 | Perlitz |
| 6,423,002 B1 | 7/2002 | Hossack |
| 6,436,046 B1 | 8/2002 | Napolitano et al. |
| 6,449,821 B1 | 9/2002 | Sudol et al. |
| 6,450,965 B2 | 9/2002 | Williams et al. |
| 6,468,216 B1 | 10/2002 | Powers et al. |
| 6,471,650 B2 | 10/2002 | Powers et al. |
| 6,475,150 B2 | 11/2002 | Haddad |
| 6,480,790 B1 | 11/2002 | Calvert et al. |
| 6,487,502 B1 | 11/2002 | Taner |
| 6,499,536 B1 | 12/2002 | Ellingsen |
| 6,508,768 B1 | 1/2003 | Hall et al. |
| 6,517,484 B1 | 2/2003 | Wilk et al. |
| 6,526,163 B1 | 2/2003 | Halmann et al. |
| 6,543,272 B1 | 4/2003 | Vitek |
| 6,547,732 B2 | 4/2003 | Jago |
| 6,551,246 B1 | 4/2003 | Ustuner et al. |
| 6,565,510 B1 | 5/2003 | Haider |
| 6,585,647 B1 | 7/2003 | Winder |
| 6,604,421 B1 | 8/2003 | Li |
| 6,614,560 B1 | 9/2003 | Silverbrook |
| 6,620,101 B2 | 9/2003 | Azzam et al. |
| 6,652,461 B1 | 11/2003 | Levkovitz |

(56) References Cited

U.S. PATENT DOCUMENTS

| | | |
|---|---|---|
| 6,668,654 B2 | 12/2003 | Dubois et al. |
| 6,672,165 B2 | 1/2004 | Rather et al. |
| 6,681,185 B1 | 1/2004 | Young et al. |
| 6,690,816 B2 | 2/2004 | Aylward et al. |
| 6,692,450 B1 | 2/2004 | Coleman |
| 6,695,778 B2 | 2/2004 | Golland et al. |
| 6,702,745 B1 | 3/2004 | Smythe |
| 6,719,693 B2 | 4/2004 | Richard |
| 6,728,567 B2 | 4/2004 | Rather et al. |
| 6,752,762 B1 | 6/2004 | DeJong et al. |
| 6,755,787 B2 | 6/2004 | Hossack et al. |
| 6,780,152 B2 | 8/2004 | Ustuner et al. |
| 6,790,182 B2 | 9/2004 | Eck et al. |
| 6,837,853 B2 | 1/2005 | Marian |
| 6,843,770 B2 | 1/2005 | Sumanaweera |
| 6,847,737 B1 | 1/2005 | Kouri et al. |
| 6,854,332 B2 | 2/2005 | Alleyne |
| 6,932,767 B2 | 8/2005 | Landry et al. |
| 7,033,320 B2 | 4/2006 | Von Behren et al. |
| 7,087,023 B2 | 8/2006 | Daft et al. |
| 7,104,956 B1 | 9/2006 | Christopher |
| 7,217,243 B2 | 5/2007 | Takeuchi |
| 7,221,867 B2 | 5/2007 | Silverbrook |
| 7,231,072 B2 | 6/2007 | Yamano et al. |
| 7,269,299 B2 | 9/2007 | Schroeder |
| 7,283,652 B2 | 10/2007 | Mendonca et al. |
| 7,285,094 B2 | 10/2007 | Nohara et al. |
| 7,313,053 B2 | 12/2007 | Wodnicki |
| 7,366,704 B2 | 4/2008 | Reading et al. |
| 7,402,136 B2 | 7/2008 | Hossack et al. |
| 7,410,469 B1 | 8/2008 | Talish et al. |
| 7,415,880 B2 | 8/2008 | Renzel |
| 7,443,765 B2 | 10/2008 | Thomenius et al. |
| 7,444,875 B1 | 11/2008 | Wu et al. |
| 7,447,535 B2 | 11/2008 | Lavi |
| 7,448,998 B2 | 11/2008 | Robinson |
| 7,466,848 B2 | 12/2008 | Metaxas et al. |
| 7,469,096 B2 | 12/2008 | Silverbrook |
| 7,474,778 B2 | 1/2009 | Shinomura et al. |
| 7,481,577 B2 | 1/2009 | Ramamurthy et al. |
| 7,491,171 B2 | 2/2009 | Barthe et al. |
| 7,497,828 B1 | 3/2009 | Wilk et al. |
| 7,497,830 B2 | 3/2009 | Li |
| 7,510,529 B2 | 3/2009 | Chou et al. |
| 7,514,851 B2 | 4/2009 | Wilser et al. |
| 7,549,962 B2 | 6/2009 | Dreschel et al. |
| 7,574,026 B2 | 8/2009 | Rasche et al. |
| 7,625,343 B2 | 12/2009 | Cao et al. |
| 7,637,869 B2 | 12/2009 | Sudol |
| 7,668,583 B2 | 2/2010 | Fegert et al. |
| 7,674,228 B2 | 3/2010 | Williams et al. |
| 7,682,311 B2 | 3/2010 | Simopoulos et al. |
| 7,699,776 B2 | 4/2010 | Walker et al. |
| 7,722,541 B2 | 5/2010 | Cai |
| 7,744,532 B2 | 6/2010 | Ustuner et al. |
| 7,750,311 B2 | 7/2010 | Daghighian |
| 7,785,260 B2 | 8/2010 | Umemura et al. |
| 7,787,680 B2 | 8/2010 | Ahn et al. |
| 7,806,828 B2 | 10/2010 | Stringer |
| 7,819,810 B2 | 10/2010 | Stringer et al. |
| 7,822,250 B2 | 10/2010 | Yao et al. |
| 7,824,337 B2 | 11/2010 | Abe et al. |
| 7,833,163 B2 | 11/2010 | Cai |
| 7,837,624 B1 | 11/2010 | Hossack et al. |
| 7,846,097 B2 | 12/2010 | Jones et al. |
| 7,850,613 B2 | 12/2010 | Stribling |
| 7,862,508 B2 | 1/2011 | Davies et al. |
| 7,876,945 B2 | 1/2011 | Lötjönen |
| 7,887,486 B2 | 2/2011 | Ustuner et al. |
| 7,901,358 B2 | 3/2011 | Mehi et al. |
| 7,914,451 B2 | 3/2011 | Davies |
| 7,919,906 B2 | 4/2011 | Cerofolini |
| 7,926,350 B2 | 4/2011 | Kröning et al. |
| 7,927,280 B2 | 4/2011 | Davidsen |
| 7,972,271 B2 | 7/2011 | Johnson et al. |
| 7,984,637 B2 | 7/2011 | Ao et al. |
| 7,984,651 B2 | 7/2011 | Randall et al. |
| 8,002,705 B1 | 8/2011 | Napolitano et al. |
| 8,007,439 B2 | 8/2011 | Specht |
| 8,057,392 B2 | 11/2011 | Hossack et al. |
| 8,057,393 B2 | 11/2011 | Yao et al. |
| 8,079,263 B2 | 12/2011 | Randall et al. |
| 8,079,956 B2 | 12/2011 | Azuma et al. |
| 8,088,067 B2 | 1/2012 | Vortman et al. |
| 8,088,068 B2 | 1/2012 | Yao et al. |
| 8,088,071 B2 | 1/2012 | Hwang et al. |
| 8,105,239 B2 | 1/2012 | Specht |
| 8,135,190 B2 | 3/2012 | Bae et al. |
| 8,157,737 B2 | 4/2012 | Zhang et al. |
| 8,182,427 B2 | 5/2012 | Wu et al. |
| 8,202,219 B2 | 6/2012 | Luo et al. |
| 8,277,383 B2 | 10/2012 | Specht |
| 8,412,307 B2 | 4/2013 | Willis et al. |
| 8,419,642 B2 | 4/2013 | Sandrin et al. |
| 8,473,239 B2 | 6/2013 | Specht et al. |
| 8,478,382 B2 | 7/2013 | Burnside et al. |
| 8,532,951 B2 | 9/2013 | Roy et al. |
| 8,634,615 B2 | 1/2014 | Brabec |
| 8,672,846 B2 | 3/2014 | Napolitano et al. |
| 2002/0035864 A1 | 3/2002 | Paltieli et al. |
| 2002/0087071 A1 | 7/2002 | Schmitz et al. |
| 2002/0111568 A1 | 8/2002 | Bukshpan |
| 2002/0161299 A1 | 10/2002 | Prater et al. |
| 2003/0028111 A1 | 2/2003 | Vaezy et al. |
| 2003/0040669 A1 | 2/2003 | Grass et al. |
| 2003/0228053 A1 | 12/2003 | Li et al. |
| 2004/0054283 A1 | 3/2004 | Corey et al. |
| 2004/0068184 A1 | 4/2004 | Trahey et al. |
| 2004/0100163 A1 | 5/2004 | Baumgartner et al. |
| 2004/0111028 A1 | 6/2004 | Abe et al. |
| 2004/0122313 A1 | 6/2004 | Moore et al. |
| 2004/0122322 A1 | 6/2004 | Moore et al. |
| 2004/0127793 A1 | 7/2004 | Mendlein et al. |
| 2004/0138565 A1 | 7/2004 | Trucco |
| 2004/0144176 A1 | 7/2004 | Yoden |
| 2004/0236217 A1 | 11/2004 | Cerwin et al. |
| 2004/0236223 A1 | 11/2004 | Barnes et al. |
| 2005/0004449 A1 | 1/2005 | Mitschke et al. |
| 2005/0053305 A1 | 3/2005 | Li et al. |
| 2005/0054910 A1 | 3/2005 | Tremblay et al. |
| 2005/0090743 A1 | 4/2005 | Kawashima et al. |
| 2005/0090745 A1 | 4/2005 | Steen |
| 2005/0111846 A1 | 5/2005 | Steinbacher et al. |
| 2005/0113694 A1 | 5/2005 | Haugen et al. |
| 2005/0124883 A1 | 6/2005 | Hunt |
| 2005/0131300 A1 | 6/2005 | Bakircioglu et al. |
| 2005/0147297 A1 | 7/2005 | McLaughlin et al. |
| 2005/0165312 A1 | 7/2005 | Knowles et al. |
| 2005/0203404 A1 | 9/2005 | Freiburger |
| 2005/0215883 A1 | 9/2005 | Hundley et al. |
| 2005/0240125 A1 | 10/2005 | Makin et al. |
| 2005/0252295 A1 | 11/2005 | Fink et al. |
| 2005/0281447 A1 | 12/2005 | Moreau-Gobard et al. |
| 2005/0288588 A1 | 12/2005 | Weber et al. |
| 2006/0062447 A1 | 3/2006 | Rinck et al. |
| 2006/0074313 A1 | 4/2006 | Slayton et al. |
| 2006/0074315 A1 | 4/2006 | Liang et al. |
| 2006/0074320 A1 | 4/2006 | Yoo et al. |
| 2006/0079759 A1 | 4/2006 | Vaillant et al. |
| 2006/0079778 A1 | 4/2006 | Mo et al. |
| 2006/0079782 A1 | 4/2006 | Beach et al. |
| 2006/0094962 A1 | 5/2006 | Clark |
| 2006/0111634 A1 | 5/2006 | Wu |
| 2006/0122506 A1 | 6/2006 | Davies et al. |
| 2006/0173327 A1 | 8/2006 | Kim |
| 2006/0262291 A1 | 11/2006 | Hess et al. |
| 2006/0262961 A1 | 11/2006 | Holsing et al. |
| 2007/0016022 A1 | 1/2007 | Blalock et al. |
| 2007/0016044 A1 | 1/2007 | Blalock et al. |
| 2007/0036414 A1 | 2/2007 | Georgescu et al. |
| 2007/0055155 A1 | 3/2007 | Owen et al. |
| 2007/0078345 A1 | 4/2007 | Mo et al. |
| 2007/0088213 A1 | 4/2007 | Poland |
| 2007/0138157 A1 | 6/2007 | Dane et al. |

(56) References Cited

U.S. PATENT DOCUMENTS

| | | |
|---|---|---|
| 2007/0161898 A1 | 7/2007 | Hao et al. |
| 2007/0161904 A1 | 7/2007 | Urbano |
| 2007/0167752 A1 | 7/2007 | Proulx et al. |
| 2007/0167824 A1 | 7/2007 | Lee et al. |
| 2007/0232914 A1 | 10/2007 | Chen et al. |
| 2007/0238985 A1 | 10/2007 | Smith et al. |
| 2007/0242567 A1 | 10/2007 | Daft et al. |
| 2008/0110261 A1 | 5/2008 | Randall et al. |
| 2008/0110263 A1 | 5/2008 | Klessel et al. |
| 2008/0112265 A1 | 5/2008 | Urbano et al. |
| 2008/0114241 A1 | 5/2008 | Randall et al. |
| 2008/0114245 A1 | 5/2008 | Randall et al. |
| 2008/0114246 A1 | 5/2008 | Randall et al. |
| 2008/0114247 A1 | 5/2008 | Urbano et al. |
| 2008/0114248 A1 | 5/2008 | Urbano et al. |
| 2008/0114249 A1 | 5/2008 | Randall et al. |
| 2008/0114250 A1 | 5/2008 | Urbano et al. |
| 2008/0114251 A1 | 5/2008 | Weymer et al. |
| 2008/0114252 A1 | 5/2008 | Randall et al. |
| 2008/0114253 A1 | 5/2008 | Randall et al. |
| 2008/0114255 A1 | 5/2008 | Schwartz et al. |
| 2008/0125659 A1 | 5/2008 | Wilser et al. |
| 2008/0181479 A1 | 7/2008 | Yang et al. |
| 2008/0183075 A1 | 7/2008 | Govari et al. |
| 2008/0188747 A1 | 8/2008 | Randall et al. |
| 2008/0188750 A1 | 8/2008 | Randall et al. |
| 2008/0194957 A1 | 8/2008 | Hoctor et al. |
| 2008/0194958 A1 | 8/2008 | Lee et al. |
| 2008/0194959 A1 | 8/2008 | Wang et al. |
| 2008/0208061 A1 | 8/2008 | Halmann |
| 2008/0242996 A1 | 10/2008 | Hall et al. |
| 2008/0249408 A1 | 10/2008 | Palmeri et al. |
| 2008/0255452 A1 | 10/2008 | Entrekin |
| 2008/0269604 A1 | 10/2008 | Boctor et al. |
| 2008/0269613 A1 | 10/2008 | Summers et al. |
| 2008/0275344 A1 | 11/2008 | Glide-Hurst et al. |
| 2008/0285819 A1 | 11/2008 | Konofagou et al. |
| 2008/0287787 A1 | 11/2008 | Sauer et al. |
| 2008/0294045 A1 | 11/2008 | Ellington et al. |
| 2008/0294050 A1 | 11/2008 | Shinomura et al. |
| 2008/0294052 A1 | 11/2008 | Wilser et al. |
| 2008/0306382 A1 | 12/2008 | Guracar et al. |
| 2008/0306386 A1 | 12/2008 | Baba et al. |
| 2008/0319317 A1 | 12/2008 | Kamiyama et al. |
| 2009/0010459 A1 | 1/2009 | Garbini et al. |
| 2009/0012393 A1 | 1/2009 | Choi |
| 2009/0016163 A1 | 1/2009 | Freeman et al. |
| 2009/0018445 A1 | 1/2009 | Schers et al. |
| 2009/0024039 A1 | 1/2009 | Wang et al. |
| 2009/0036780 A1 | 2/2009 | Abraham |
| 2009/0043206 A1 | 2/2009 | Towfiq et al. |
| 2009/0048519 A1 | 2/2009 | Hossack et al. |
| 2009/0069681 A1 | 3/2009 | Lundberg et al. |
| 2009/0069686 A1 | 3/2009 | Daft et al. |
| 2009/0069692 A1 | 3/2009 | Cooley et al. |
| 2009/0099483 A1 | 4/2009 | Rybyanets |
| 2009/0112095 A1 | 4/2009 | Daigle |
| 2009/0131797 A1 | 5/2009 | Jeong et al. |
| 2009/0143680 A1 | 6/2009 | Yao et al. |
| 2009/0148012 A1 | 6/2009 | Altmann et al. |
| 2009/0150094 A1 | 6/2009 | Van Velsor et al. |
| 2009/0182237 A1 | 7/2009 | Angelsen et al. |
| 2009/0198134 A1 | 8/2009 | Hashimoto et al. |
| 2009/0203997 A1 | 8/2009 | Ustuner |
| 2009/0208080 A1 | 8/2009 | Grau et al. |
| 2009/0259128 A1 | 10/2009 | Stribling |
| 2009/0264760 A1 | 10/2009 | Lazebnik et al. |
| 2009/0306510 A1 | 12/2009 | Hashiba et al. |
| 2009/0326379 A1 | 12/2009 | Daigle et al. |
| 2010/0010354 A1 | 1/2010 | Skerl et al. |
| 2010/0016725 A1 | 1/2010 | Thiele |
| 2010/0063397 A1 | 3/2010 | Wagner |
| 2010/0063399 A1 | 3/2010 | Walker et al. |
| 2010/0069751 A1 | 3/2010 | Hazard et al. |
| 2010/0069756 A1 | 3/2010 | Ogasawara et al. |
| 2010/0106431 A1 | 4/2010 | Baba et al. |
| 2010/0109481 A1 | 5/2010 | Buccafusca |
| 2010/0121193 A1 | 5/2010 | Fukukita et al. |
| 2010/0121196 A1 | 5/2010 | Hwang et al. |
| 2010/0130855 A1 | 5/2010 | Lundberg et al. |
| 2010/0168566 A1 | 7/2010 | Bercoff et al. |
| 2010/0168578 A1 | 7/2010 | Garson, Jr. et al. |
| 2010/0174194 A1 | 7/2010 | Chiang et al. |
| 2010/0217124 A1 | 8/2010 | Cooley |
| 2010/0240994 A1 | 9/2010 | Zheng |
| 2010/0249570 A1 | 9/2010 | Carson et al. |
| 2010/0249596 A1 | 9/2010 | Magee |
| 2010/0256488 A1 | 10/2010 | Kim et al. |
| 2010/0262013 A1 | 10/2010 | Smith et al. |
| 2010/0266176 A1 | 10/2010 | Masumoto et al. |
| 2010/0286525 A1 | 11/2010 | Osumi |
| 2010/0286527 A1 | 11/2010 | Cannon et al. |
| 2010/0310143 A1 | 12/2010 | Rao et al. |
| 2010/0324418 A1 | 12/2010 | El-Aklouk et al. |
| 2010/0324423 A1 | 12/2010 | El-Aklouk et al. |
| 2010/0329521 A1 | 12/2010 | Beymer et al. |
| 2011/0005322 A1 | 1/2011 | Ustuner |
| 2011/0016977 A1 | 1/2011 | Guracar |
| 2011/0021920 A1 | 1/2011 | Shafir et al. |
| 2011/0021923 A1 | 1/2011 | Daft et al. |
| 2011/0033098 A1 | 2/2011 | Richter et al. |
| 2011/0044133 A1 | 2/2011 | Tokita |
| 2011/0066030 A1 | 3/2011 | Yao |
| 2011/0098565 A1 | 4/2011 | Masuzawa |
| 2011/0112400 A1 | 5/2011 | Emery et al. |
| 2011/0112404 A1 | 5/2011 | Gourevitch |
| 2011/0125017 A1 | 5/2011 | Ramamurthy et al. |
| 2011/0178400 A1 | 7/2011 | Specht et al. |
| 2011/0201933 A1 | 8/2011 | Specht et al. |
| 2011/0270088 A1 | 11/2011 | Shiina |
| 2012/0036934 A1 | 2/2012 | Kröning et al. |
| 2012/0057428 A1 | 3/2012 | Specht et al. |
| 2012/0095343 A1 | 4/2012 | Smith et al. |
| 2012/0095347 A1 | 4/2012 | Adam et al. |
| 2012/0116226 A1 | 5/2012 | Specht |
| 2012/0137778 A1 | 6/2012 | Kitazawa et al. |
| 2012/0165670 A1 | 6/2012 | Shi et al. |
| 2012/0179044 A1 | 7/2012 | Chiang et al. |
| 2012/0243763 A1 | 9/2012 | Wen et al. |
| 2013/0035595 A1 | 2/2013 | Specht |
| 2013/0131516 A1 | 5/2013 | Katsuyama |
| 2013/0144166 A1 | 6/2013 | Specht et al. |
| 2013/0172743 A1 | 7/2013 | Brewer et al. |
| 2013/0261463 A1 | 10/2013 | Chiang et al. |

FOREIGN PATENT DOCUMENTS

| | | |
|---|---|---|
| EP | 2058796 A2 | 5/2009 |
| EP | 2101191 A2 | 9/2009 |
| EP | 2182352 A2 | 5/2010 |
| EP | 2187813 A1 | 5/2010 |
| EP | 2198785 A1 | 6/2010 |
| EP | 1757955 B1 | 11/2010 |
| EP | 2325672 A1 | 5/2011 |
| EP | 2356941 A1 | 8/2011 |
| EP | 1979739 | 10/2011 |
| EP | 2294400 | 2/2012 |
| EP | 1840594 B1 | 6/2012 |
| EP | 1850743 B1 | 12/2012 |
| EP | 1594404 B1 | 9/2013 |
| EP | 2026280 B1 | 10/2013 |
| FR | 2851662 A1 | 8/2004 |
| JP | S49-11189 A | 1/1974 |
| JP | S54-44375 A | 4/1979 |
| JP | S55-103839 A | 8/1980 |
| JP | 59-101143 | 6/1984 |
| JP | S59-174151 A | 10/1984 |
| JP | S60-13109 U | 1/1985 |
| JP | S60-68836 A | 4/1985 |
| JP | 501431 | 5/1990 |
| JP | 4-67856 | 3/1992 |
| JP | 05-042138 A | 2/1993 |
| JP | 6-125908 | 5/1994 |
| JP | 7-051266 A | 2/1995 |

(56) References Cited

FOREIGN PATENT DOCUMENTS

| | | |
|---|---|---|
| JP | 08-252253 | 10/1996 |
| JP | 9-103429 A | 4/1997 |
| JP | 9-201361 A | 8/1997 |
| JP | 10-216128 A | 8/1998 |
| JP | 11-089833 A | 4/1999 |
| JP | 2001-245884 A | 9/2001 |
| JP | 2002-209894 A | 7/2002 |
| JP | 2002-253548 | 9/2002 |
| JP | 2002-253549 A | 9/2002 |
| JP | 2004-167092 A | 6/2004 |
| JP | 2004-215987 | 8/2004 |
| JP | 2004-337457 | 12/2004 |
| JP | 2004-351214 | 12/2004 |
| JP | 2005-523792 | 8/2005 |
| JP | 2005-526539 | 9/2005 |
| JP | 2006-122657 A | 5/2006 |
| JP | 2008-122209 | 5/2008 |
| JP | 2008-513763 A | 5/2008 |
| JP | 2008-259541 A | 10/2008 |
| JP | 20105375 | 1/2010 |
| KR | 1020090103408 A | 10/2009 |
| WO | WO 92/18054 A1 | 10/1992 |
| WO | WO 98/00719 A2 | 1/1998 |
| WO | WO02/084594 A2 | 10/2002 |
| WO | WO2005/009245 A1 | 2/2005 |
| WO | WO 2006/114735 A1 | 11/2006 |
| WO | WO 2007/127147 A2 | 11/2007 |
| WO | WO2009/060182 A2 | 5/2009 |
| WO | WO 2010/017445 A2 | 2/2010 |
| WO | WO 2010/095094 A1 | 8/2010 |
| WO | WO2011/057252 A1 | 5/2011 |
| WO | WO2011/064688 A1 | 6/2011 |
| WO | WO2011/100697 A1 | 8/2011 |
| WO | WO2011/123529 A1 | 10/2011 |

OTHER PUBLICATIONS

Call et al.; U.S. Appl. No. 13/971,689 entitled "Ultrasound Imaging System Memory Architecture," filed Aug. 20, 2013.

Hendee et al.; Medical Imaging Physics; Wiley-Liss, Inc. 4th Edition; Chap. 19-22; pp. 303-353; © 2002 (year of pub. sufficiently earlier than effective US filed and any foreign priority date).

Wikipedia; Point cloud; 2 pages; Nov. 24, 2014; retrieved from the internet (https://en.wikipedia.org/w/index.php?title=Point_cloud&oldid=472583138).

Smith et al.; U.S. Appl. No. 14/526,186 entitled "Universal multiple aperture medical ultrasound probe," filed Oct. 28, 2014.

Smith et al.; U.S. Appl. No. 14/595,083 entitled "Concave ultrasound transducers and 3D arrays," filed Jan. 12, 2015.

Smith et al.; U.S. Appl. No. 14/210,015 entitled "Alignment of ultrasound transducer arrays and multiple aperture probe assembly," filed Mar. 13, 2014.

Specht et al.; U.S. Appl. No. 14/279,052 entitled "Ultrasound imaging using apparent point-source transmit transducer," filed May 15, 2014.

Cristianini et al.; An Introduction to Support Vector Machines; Cambridge University Press; pp. 93-111; Mar. 2000.

Du et al.; User parameter free approaches to multistatic adaptive ultrasound imaging; 5th IEEE International Symposium; pp. 1287-1290, May 2008.

Feigenbaum, Harvey, M.D.; Echocardiography; Lippincott Williams & Wilkins; Philadelphia; 5th Ed.; pp. 428, 484; Feb. 1994.

Haykin, Simon; Neural Networks: A Comprehensive Foundation (2nd Ed.); Prentice Hall; pp. 156-187; Jul. 16, 1998.

Kramb et al,.; Considerations for using phased array ultrasonics in a fully automated inspection system. Review of Quantitative Nondestructive Evaluation, vol. 23, ed. D. O. Thompson and D. E. Chimenti, pp. 817-825, (year of publication is sufficiently earlier than the effective U.S. filed and any foreign priority date) 2004.

Ledesma-Carbayo et al.; Spatio-temporal nonrigid registration for ultrasound cardiac motion estimation; IEEE Trans. On Medical Imaging; vol. 24; No. 9; Sep. 2005.

Leotta et al.; Quantitative three-dimensional echocardiography by rapid imaging . . . ; J American Society of Echocardiography; vol. 10; No. 8; ppl 830-839; Oct. 1997.

Morrison et al.; A probabilistic neural network based image segmentation network for magnetic resonance images; Proc. Conf. Neural Networks; Baltimore, MD; vol. 3; pp. 60-65; Jun. 1992.

Nadkarni et al.; Cardiac motion synchronization for 3D cardiac ultrasound imaging; Ph.D. Dissertation, University of Western Ontario; Jun. 2002.

Press et al.; Cubic spline interpolation; §3.3 in "Numerical Recipes in FORTRAN: The Art of Scientific Computing", 2nd Ed.; Cambridge, England; Cambridge University Press; pp. 107-110; Sep. 1992.

Sakas et al.; Preprocessing and volume rendering of 3D ultrasonic data; IEEE Computer Graphics and Applications; pp. 47-54, Jul. 1995.

Sapia et al.; Deconvolution of ultrasonic waveforms using an adaptive wiener filter; Review of Progress in Quantitative Nondestructive Evaluation; vol. 13A; Plenum Press; pp. 855-862; (year of publication is sufficiently earlier than the effective U.S. filing date and any foreign priority date) 1994.

Sapia et al.; Ultrasound image deconvolution using adaptive inverse filtering; 12 IEEE Symposium on Computer-Based Medical Systems, CBMS, pp. 248-253; Jun. 1999.

Sapia, Mark Angelo; Multi-dimensional deconvolution of optical microscope and ultrasound imaging using adaptive least-mean-square (LMS) inverse filtering; Ph.D. Dissertation; University of Connecticut; Jan. 2000.

Smith et al.; High-speed ultrasound volumetric imaging system. 1. Transducer design and beam steering; IEEE Trans. Ultrason., Ferroelect., Freq. Contr.; vol. 38; pp. 100-108; Mar. 1991.

Specht et al.; Deconvolution techniques for digital longitudinal tomography; SPIE; vol. 454; presented at Application of Optical Instrumentation in Medicine XII; pp. 319-325; Jun. 1984.

Specht et al.; Experience with adaptive PNN and adaptive GRNN; Proc. IEEE International Joint Conf. on Neural Networks; vol. 2; pp. 1203-1208; Orlando, FL; Jun. 1994.

Specht, D.F.; A general regression neural network; IEEE Trans. On Neural Networks; vol. 2.; No. 6; Nov. 1991.

Specht, D.F.; Blind deconvolution of motion blur using LMS inverse filtering; Lockheed Independent Research (unpublished); Jun. 23, 1975.

Specht, D.F.; Enhancements to probabilistic neural networks; Proc. IEEE International Joint Conf. on Neural Networks; Baltimore, MD; Jun. 1992.

Specht, D.F.; GRNN with double clustering; Proc. IEEE International Joint Conf. Neural Networks; Vancouver, Canada; Jul. 16-21, 2006.

Specht, D.F.; Probabilistic neural networks; Pergamon Press; Neural Networks; vol. 3; pp. 109-118; Feb. 1990.

Von Ramm et al.; High-speed ultrasound volumetric imaging—System. 2. Parallel processing and image display; IEEE Trans. Ultrason., Ferroelect., Freq Contr.; vol. 38; pp. 109-115; Mar. 1991.

Wells, P.N.T.; Biomedical ultrasonics; Academic Press; London, New York, San Francisco; pp. 124-125; Mar. 1977.

Widrow et al.; Adaptive signal processing; Prentice-Hall; Englewood Cliffs, NJ; pp. 99-116; Mar. 1985.

Specht et al.; U.S. Appl. No. 13/773,340 entitled "Determining Material Stiffness Using Multiple Aperture Ultrasound," filed Feb. 21, 2013.

Call et al.; U.S. Appl. No. 13/850,823 entitled "Systems and methods for improving ultrasound image quality by applying weighting factors," filed Mar. 26, 2013.

Specht et al.; U.S. Appl. No. 14/078,311 entitled "Imaging with Multiple Aperture Medical Ultrasound and Synchronization of Add-On Systems," filed Nov. 12, 2013.

Specht, D. F.; U.S. Appl. No. 14/157,257 entitled "Method and Apparatus to Produce Ultrasonic Images Using Multiple Apertures," filed Jan. 16, 2014.

Li et al.; An efficient speckle tracking algorithm for ultrasonic imaging; 24; pp. 215-228; Oct. 1, 2002.

(56) References Cited

OTHER PUBLICATIONS

UCLA Academic Technology; SPSS learning module: How can I analyze a subset of my data; 6 pages; retrieved from the Internet (http://www.ats.ucla.edu/stat/spss/modules/subset_analyze.htm) Nov. 26, 2001.

Wikipedia; Curve fitting; 5 pages; retrieved from the internet (http:en.wikipedia.org/wiki/Curve_fitting) Dec. 19, 2010.

Wikipedia; Speed of sound; 17 pages; retrieved from the Internet (http: en.wikipedia.org/wiki/Speed_of_sound) Aug. 29, 2015.

Carson et al.; Measurement of photoacoustic transducer position by robotic source placement and nonlinear parameter estimation; Biomedical Optics (BIOS); International Society for Optics and Photonics (9th Conf. on Biomedical Thermoacoustics, Optoacoustics, and Acousto-optics; vol. 6856; 9 pages; Feb 28, 2008.

Chen et al.; Maximum-likelihood source localization and unknown sensor location estimation for wideband signals in the near-field; IEEE Transactions on Signal Processing; 50(8); pp. 1843-1854; Aug. 2002.

Chen et al.; Source localization and tracking of a wideband source using a randomly distributed beamforming sensor array; International Journal of High Performance Computing Applications; 16(3); pp. 259-272; Fall 2002.

Fernandez et al.; High resolution ultrasound beamforming using synthetic and adaptive imaging techniques; Proceedings IEEE International Symposium on Biomedical Imaging; Washington, D.C.; pp. 433-436; Jul. 7-10, 2002.

Gazor et al.; Wideband multi-source beamforming with array location calibration and direction finding; Conference on Acoustics, Speech and Signal Processing Icassp-95; Detroit, MI; vol. 3 IEEE; pp. 1904-1907; May 9-12, 1995.

Heikkila et al.; A four-step camera calibration procedure with implicit image correction; Proceedings IEEE Computer Scociety Conference on Computer Vision and Pattern Recognition; San Juan; pp. 1106-1112; Jun. 17-19,1997.

Hsu et al.; Real-time freehand 3D ultrasound calibration; CUED/F-INFENG/TR 565; Department of Engineering, University of Cambridge, United Kingdom; 14 pages; Sep. 2006.

Khamene et al.; A novel phantom-less spatial and temporal ultrasound calibration method; Medical Image Computing and Computer-Assisted Intervention—MICCAI (Proceedings 8th Int. Conf.); Springer Berlin Heidelberg; Palm Springs, CA; pp. 65-72; Oct. 26-29, 2005.

Slavine et al.; Construction, calibration and evaluation of a tissue phantom with reproducible optical properties for investigations in light emission tomography; Engineering in Medicine and Biology Workshop; Dallas, TX; IEEE pp. 122-125; Nov. 11-12, 2007.

Wang et al.; Photoacoustic tomography of biological tissues with high cross-section resolution: reconstruction and experiment; Medical Physics; 29(12); pp. 2799-2805; Dec. 2002.

\* cited by examiner

PHANTOM END VIEW

ASSEMBLED TEST FIXTURE IN TANK

FIRST REFERENCE IS LC OR RC
FINAL REFERENCE IS CENTER OF CENTER PROBE (CC)

MULTIPLE APERTURE ULTRASOUND ARRAY ALIGNMENT FIXTURE

CROSS REFERENCE TO RELATED APPLICATIONS

This application is a continuation of U.S. patent application Ser. No. 12/760,327, filed Apr. 14, 2010, now U.S. Pat. No. 8,473,239, which application claims the benefit of U.S. Provisional Patent Application No. 61/169,200, filed Apr. 14, 2009, titled "ALIGNMENT AND FIXTURING OF A UNIVERSAL MULTIPLE APERTURE MEDICAL ULTRASOUND TRANSDUCER", which is herein incorporated by reference.

This application is related to U.S. patent application Ser. No. 11/532,013, filed Sep. 14, 2006, now U.S. Pat. No. 8,105,239, which claims priority to U.S. Provisional Patent Application No. 60/765,887, filed Feb. 6, 2006; and is related to U.S. patent application Ser. No. 11/865,501, filed Oct. 1, 2007, now U.S. Pat. No. 8,007,439, which claims priority to U.S. Provisional Patent Application No. 60/862,951, filed Oct. 25, 2006, and U.S. Provisional Patent Application No. 60/940,261, filed May 25, 2007; and is related to U.S. Provisional Patent Application Nos. 61/169,251, filed Apr. 14, 2009, and 61/169,221, filed Apr. 14, 2009; all of which are herein incorporated by reference.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention relates generally to imaging techniques used in medicine, and more particularly to medical ultrasound, and still more particularly to an apparatus for producing ultrasonic images using multiple apertures.

BACKGROUND OF THE INVENTION

In order to insonify the body tissues, a beam formed either by a phased array or a shaped transducer is scanned over the tissues to be examined. Traditionally, the same transducer or array is used to detect the returning echoes. This design configuration lies at the heart of one of the most significant limitations in the use of ultrasonic imaging for medical purposes; namely, poor lateral resolution. Theoretically, the lateral resolution could be improved by increasing the aperture of the ultrasonic probe, but the practical problems involved with aperture size increase have kept apertures small and lateral resolution poor. Unquestionably, ultrasonic imaging has been very useful even with this limitation, but it could be more effective with better resolution.

In the practice of cardiology, for example, the limitation on single aperture size is dictated by the space between the ribs (the intercostal spaces). For scanners intended for abdominal and other use, the limitation on aperture size is not so obvious, but it is a serious limitation nevertheless. The problem is that it is difficult to know the exact position of the elements of a large apparatus with multiple and separate physical points of contact ("footprints") on the patient. For optimum performance, all of the separated transmit and receive elements should be in the same scan plane. In addition, each element position must be known to within $\frac{1}{10}$ wavelength (for example, 0.03 mm at 3 MHz). With conventional ultrasound probes, regardless of array vertical displacement or integration (e.g., 1.5D or 2D), there has never been a need to solve alignment and position issues between multiple arrays or multiple individual elements. The methods and apparatus included here teach how to solve these problems for Universal Multiple Aperture ultrasound probes.

In constructing and maintaining a Universal Multiple Aperture Probe using a combination of two or more individual arrays, attention must be paid to each array's ultrasound beam displacement relative to a central array Z axis. The displacement or rotational axes referred to are X, Y and Z. X varies about the longitudinal array axis, Y varies about the central array axes, also termed twist, and Z varies about the transverse or lateral array axis. A fixture and method for measuring the variation of each array was developed and implemented.

Element position is equally important as displacement from the central array Z axis. The positional relationship of each array element to every other element needs to be established within an individual array and from array to array.

The type of crystal used in each array is irrelevant. That is, any one, one and a half, or two dimensional crystal arrays (1D, 1.5D, 2D, such as a piezoelectric array) and all types of Capacitive Micromachined Ultrasonic Transducers (CMUT) can be utilized in multi-aperture configurations.

SUMMARY OF THE INVENTION

The present invention relates to a system for measuring and aligning the positions of transducer elements in a multi-aperture ultrasound probe, comprising an alignment assembly configured to hold a plurality of transducer elements, a test block, an ultrasonic sensor configured to receive ultrasonic pulses through the test block from at least one of the plurality of transducer elements, and a controller configured to evaluate data from the ultrasonic sensor and provide transducer calibration data.

In some embodiments, the test block comprises a tank filled with a liquid having a known speed of sound. In other embodiments, the test block comprises a tank filled with a gelatinous material having known speed of sound. In additional embodiments, the test block comprises a solid block having a known speed of sound.

The system can further comprise a signal generator configured to excite at least one of the plurality of transducer elements to transmit ultrasonic pulses. In some embodiments, the signal generator is configured to excite the plurality of transducer elements with a short (wideband) pulse. In other embodiments, the signal generator is configured to excite the plurality of transducer elements with a spread spectrum waveform. In additional embodiments, the signal generator is configured to excite at least one of the plurality of transducer elements with a chirp waveform.

In one embodiment, the alignment assembly comprises an automated alignment assembly configured to automatically align the plurality of transducer elements based on the transducer calibration data from the controller. The alignment assembly can comprise at least one stepper motor and a stepper motor controller, for example. In some embodiments, the stepper motor controller drives the at least one stepper motor to align the transducer element.

In other embodiments, the alignment assembly comprises a manual alignment assembly. The manual alignment assembly can include manual controls configured to manipulate the plurality of transducer elements in the x, y, and z axes.

In some embodiments, the controller runs algorithms configured to detect relative elapsed times to a plurality of receiving transducer elements disposed on the ultrasonic sensor. In other embodiments, the controller runs algorithms configured to compute complete transit times from at least one of the plurality of transducer elements to a plurality of receiving transducer elements disposed on the ultrasonic sensor. In some embodiments, the controller runs algorithms configured to compute the relative position of the plurality of transducer elements based on the transducer calibration data.

In some embodiments, the system further comprises a graphical user interface configured to display the transducer calibration data.

In other embodiments, the alignment assembly is configured to hold a probe containing the plurality of transducer elements.

In some embodiments, the ultrasonic sensor includes a plurality of receiving transducer elements.

In additional embodiments, the controller is configured to digitize and store the received ultrasonic pulses.

A system for measuring and reporting the positions of transducer elements in a multi-aperture ultrasound probe is also provided, comprising a plurality of transducer elements, a calibration assembly configured to hold the plurality of transducer elements, a test block, an ultrasonic sensor configured to receive ultrasonic pulses through the test block from at least one of the plurality of transducer elements, and a controller configured to evaluate data from the ultrasonic sensor and provide transducer calibration data.

In some embodiments, the test block comprises a tank filled with a liquid having a known speed of sound. In other embodiments, the test block comprises a tank filled with a gelatinous material having known speed of sound. In additional embodiments, the test block comprises a solid block having a known speed of sound.

In some embodiments, the calibration assembly is configured to automatically determine the relative positions of the plurality of transducer elements based on the transducer calibration data from the controller.

In one embodiment, the controller runs algorithms configured to detect relative elapsed times to a plurality of receiving transducer elements disposed on the ultrasonic sensor. In other embodiments, the controller runs algorithms configured to compute complete transit times from the relative elapsed times. In additional embodiments, the controller runs algorithms configured to compute the relative position of the plurality of transducer elements based on the transducer calibration data.

In some embodiments, the system further comprises a graphical user interface configured to display the transducer calibration data.

In another embodiment, the system further comprises memory in the multi-aperture ultrasound probe configured to record the transducer calibration data.

A method is also provided for measuring and aligning the positions of transducer elements in a multi-aperture ultrasound probe, comprising mounting a plurality of transducer elements in an alignment assembly, transmitting ultrasonic pulses through a test block from at least one of the plurality of transducer elements, receiving the ultrasonic pulses with an ultrasonic sensor, and evaluating the received ultrasonic pulses from the ultrasonic sensor with a controller to provide transducer calibration data.

In some embodiments, the method further comprises aligning the plurality of transducer elements based on the transducer calibration data.

In other embodiments, the method comprises automatically aligning the plurality of transducer elements based on the transducer calibration data. In other embodiments, the method comprises manually aligning the plurality of transducer elements based on the transducer calibration data.

In some embodiments, the controller runs an algorithm configured to detect relative elapsed times to a plurality of receiving transducer elements disposed on the ultrasonic sensor. In other embodiments, the controller runs an algorithm configured to compute complete transit times from the transducer element to a receiving transducer element disposed on the ultrasonic sensor. In additional embodiments, the controller runs an algorithm configured to compute the relative position of the plurality of transducer elements based on the transducer calibration data.

DETAILED DESCRIPTION OF THE INVENTION

Figure 1:
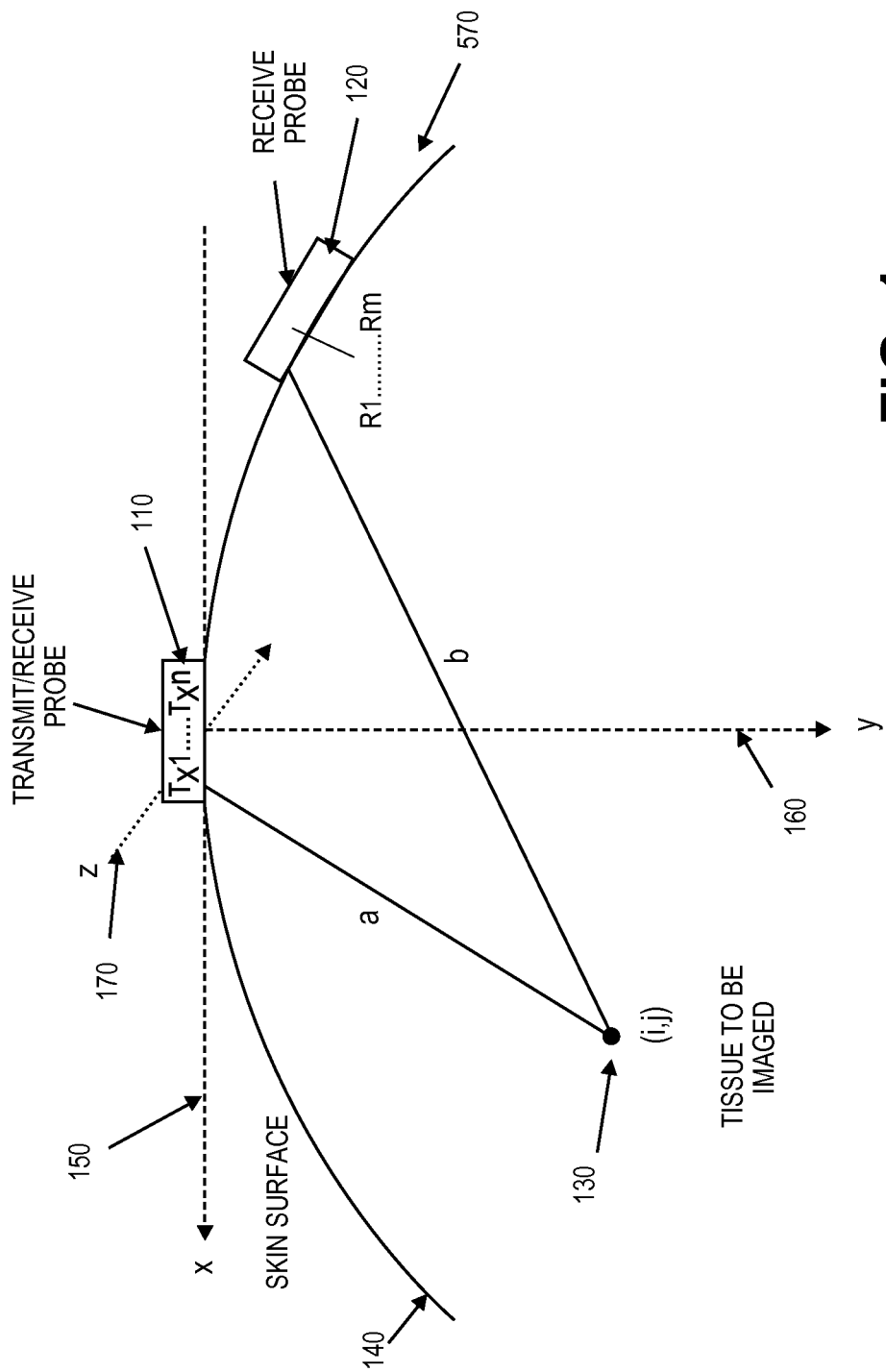
FIG. 1 illustrates a two-aperture system.

A Multiple Aperture Ultrasound Imaging (MAUI) Probe or Transducer can vary by medical application. That is, a general radiology probe can contain multiple transducers that maintain separate physical points of contact with the patient's skin, allowing multiple physical apertures. A cardiac probe may contain as few as two transmitters and receivers where the probe fits simultaneously between two or more intercostal spaces. An intracavity version of the probe, will space transmit and receive transducers along the length of the wand, while an intravenous version will allow transducers to be located on the distal length the catheter and separated by mere millimeters. In all cases, operation of multiple aperture ultrasound transducers can be greatly enhanced if they are constructed so that the elements of the arrays are aligned within a particular scan plane.

One aspect of the invention solves the problem of constructing a multiple aperture probe that functionally houses multiple transducers which may not be in alignment relative to each other. The solution involves bringing separated elements or arrays of elements into alignment within a known scan plane. The separation can be a physical separation or simply a separation in concept wherein some of the elements of the array can be shared for the two (transmitting or receiving) functions. A physical separation, whether incorporated in the construction of the probe's casing, or accommodated via an articulated linkage, is also important for wide apertures to accommodate the curvature of the body or to avoid non-echogenic tissue or structures (such as bone).

Any single omni-directional receive element (such as a single crystal pencil array) can gather information necessary to reproduce a two-dimensional section of the body. In some embodiments, a pulse of ultrasound energy is transmitted along a particular path; the signal received by the omni-directional probe can be recorded into a line of memory. When the process for recording is complete for all of the lines in a sector scan, the memory can be used to reconstruct the image.

In other embodiments, acoustic energy is intentionally transmitted to as wide a two-dimensional slice as possible. Therefore all of the beam formation must be achieved by the software or firmware associated with the receive arrays. There are several advantages to doing this: 1) It is impossible to focus tightly on transmit because the transmit pulse would have to be focused at a particular depth and would be somewhat out of focus at all other depths, and 2) An entire two-dimensional slice can be insonified with a single transmit pulse.

Omni-directional probes can be placed almost anywhere on or in the body: in multiple or intercostal spaces, the suprasternal notch, the substernal window, multiple apertures along the abdomen and other parts of the body, on an intracavity probe or on the end of a catheter.

The construction of the individual transducer elements used in the apparatus is not a limitation of use in multi-aperture systems. Any one, one and a half, or two dimensional crystal arrays (1D, 1.5D, 2D, such as a piezoelectric array) and all types of Capacitive Micromachined Ultrasonic Transducers (CMUT) can be utilized in multi-aperture configurations to improve overall resolution and field of view.

Transducers can be placed either on the image plane, off of it, or any combination. When placed away from the image plane, omni-probe information can be used to narrow the thickness of the sector scanned. Two-dimensional scanned data can best improve image resolution and speckle noise reduction when it is collected from within the same scan plane.

Greatly improved lateral resolution in ultrasound imaging can be achieved by using probes from multiple apertures. The large effective aperture (the total aperture of the several sub apertures) can be made viable by compensation for the variation of speed of sound in the tissue. This can be accomplished in one of several ways to enable the increased aperture to be effective rather than destructive.

The simplest multi-aperture system consists of two apertures, as shown in FIG. 1. One aperture could be used entirely for transmit elements 110 and the other for receive elements 120. Transmit elements can be interspersed with receive elements, or some elements could be used both for transmit and receive. In this example, the probes have two different lines of sight to the tissue to be imaged 130. That is, they maintain two separate physical apertures on the surface of the skin 140. Multiple Aperture Ultrasonic Transducers are not limited to use from the surface of the skin, they can be used anywhere in or on the body to include intracavity and intravenous probes. In transmit/receive probe 110, the positions of the individual elements $T_x1$ through $T_xn$ can be measure in three different axes. This illustration shows the probe perpendicular to the x axis 150, so each element would have a different position x and the same position y on the y axis 160. However, the y axis positions of elements in probe 120 would be different since it is angled down. The z axis 170 comes in or out of the page and is very significant in determine whether an element is in or out of the scan plane.

Referring to FIG. 1, suppose that a Transmit Probe containing ultrasound transmitting elements T1, T2, . . . Tn 110 and a Receive Probe 120 containing ultrasound receive elements R1, R2, . . . Rm are placed on the surface of a body to be examined (such as a human or animal). Both probes can be sensitive to the same plane of scan, and the mechanical position of each element of each probe is known precisely relative to a common reference such as one of the probes. In one embodiment, an ultrasound image can be produced by insonifying the entire region to be imaged (e.g., a plane through the heart, organ, tumor, or other portion of the body) with a transmitting element (e.g., transmit element $T_x1$), and then "walking" down the elements on the Transmit probe (e.g., $T_x2$, . . . $T_xn$) and insonifying the region to be imaged with each of the transmit elements. Individually, the images taken from each transmit element may not be sufficient to provide a high resolution image, but the combination of all the images can provide a high resolution image of the region to be imaged. Then, for a scanning point represented by coordinates (i,j) it is a simple matter to calculate the total distance "a" from a particular transmit element $T_xn$ to an element of tissue at (i,j) 130 plus the distance "b" from that point to a particular receive element. With this information, one could begin rendering a map of scatter positions and amplitudes by tracing the echo amplitude to all of the points for the given locus.

Figure 2:
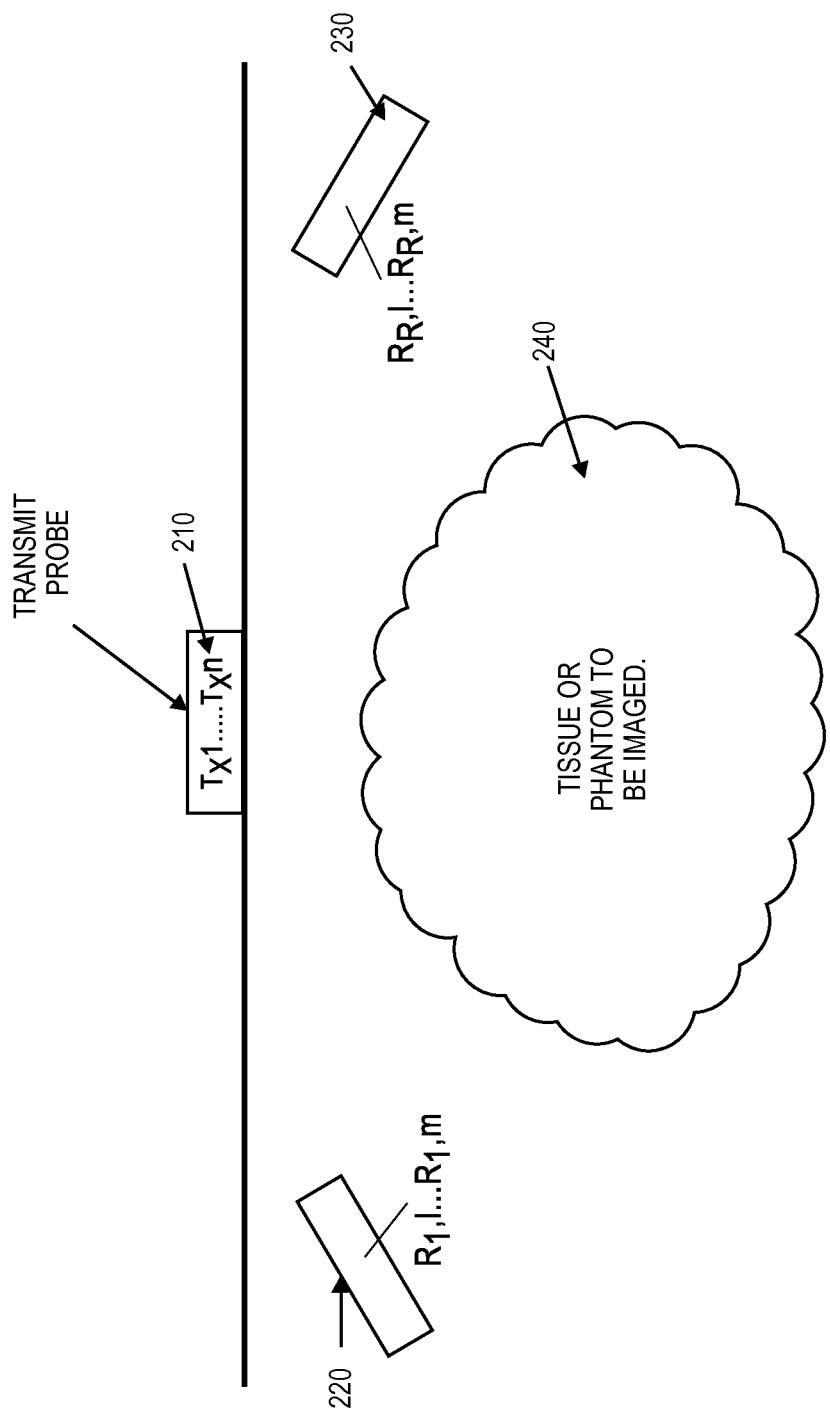
FIG. 2 illustrates a three-aperture system.

Another multi-aperture system is shown FIG. 2 and consists of transducer elements in three apertures. In one concept, elements in the center aperture 210 can be used for transmit and then elements in the left 220 and right 230 apertures can be used for receive. Another possibility is that elements in all three apertures can be used for both transmit and receive, although the compensation for speed of sound variation would be more complicated under these conditions. Positioning elements or arrays around the tissue to be imaged 240 provides much more data than simply having a single probe 210 over the top of the tissue.

Figure 3:
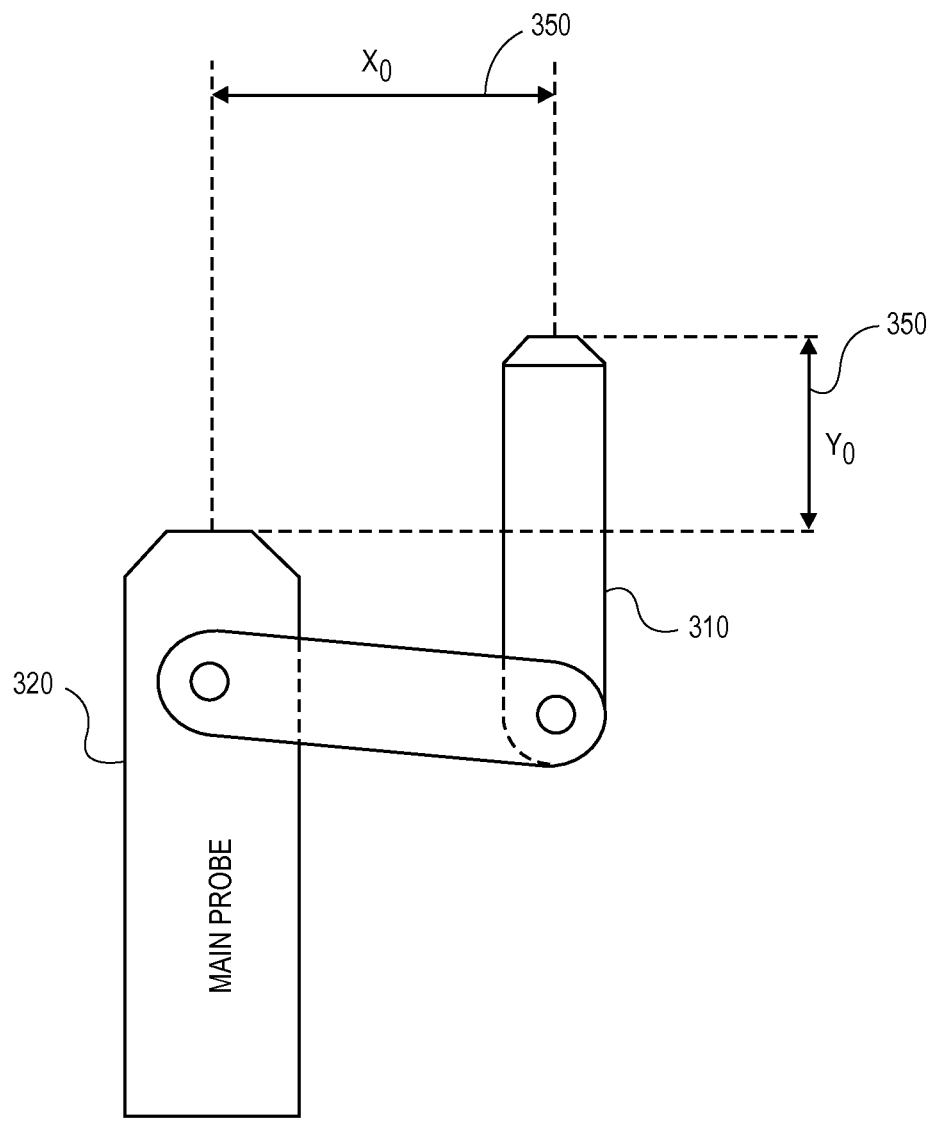
FIG. 3 is a schematic diagram showing a possible fixture for positioning an omni-directional probe relative to the main probe.
Figure 4:
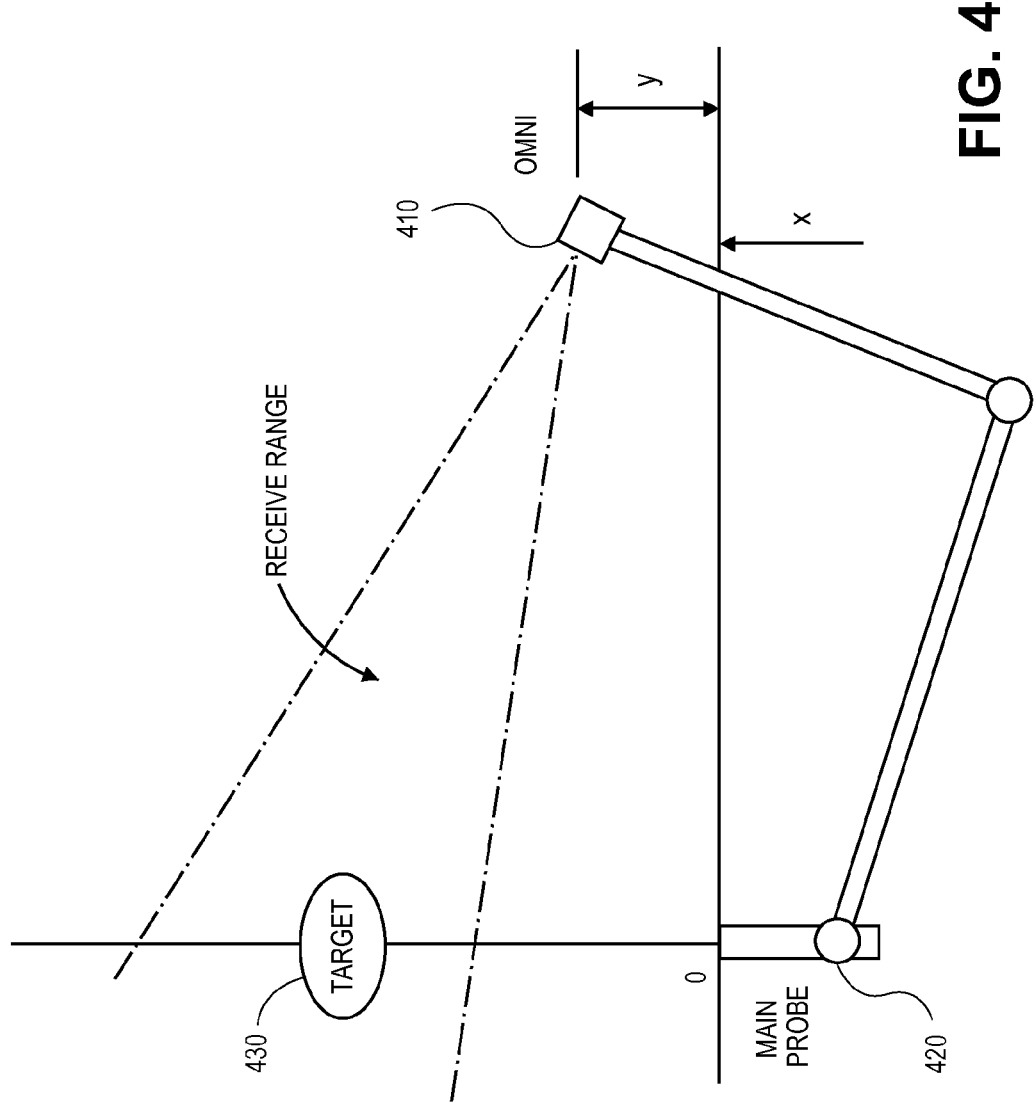
FIG. 4 is a schematic diagram showing a non-instrumented linkage for two probes.

The Multiple Aperture Ultrasonic Imaging methods described herein are dependent on a probe apparatus that allows the position of every element to be known and reports those positions to any new apparatus the probe becomes attached. FIGS. 3 and 4 demonstrate how a single omni-probe 310 or 410 can be attached to a main transducer (phased array or otherwise) so as to collect data, or conversely, to act as a transmitter where the main probe then becomes a receiver. In both of these embodiments the omni-probe is already aligned within the scan plan. Therefore, only the x and y positions 350 need be calculated and transmitted to the processor. It is also possible to construct a probe with the omni-probe out of the scan plane for better transverse focus.

An aspect of the omni-probe apparatus includes returning echoes from a separate relatively non-directional receive transducer 310 and 410 located away from the insonifying probe transmit transducer 320 and 420, and the non-directional receive transducer can be placed in a different acoustic window from the insonifying probe. The omni-directional probe can be designed to be sensitive to a wide field of view for this purpose.

The echoes detected at the omni-probe may be digitized and stored separately. If the echoes detected at the omni-probe (310 in FIG. 3 and 410 in FIG. 4) are stored separately for every pulse from the insonifying transducer, it is surprising to note that the entire two-dimensional image can be formed from the information received by the one omni. Additional copies of the image can be formed by additional omnidirectional probes collecting data from the same set of insonifying pulses.

Figure 5:
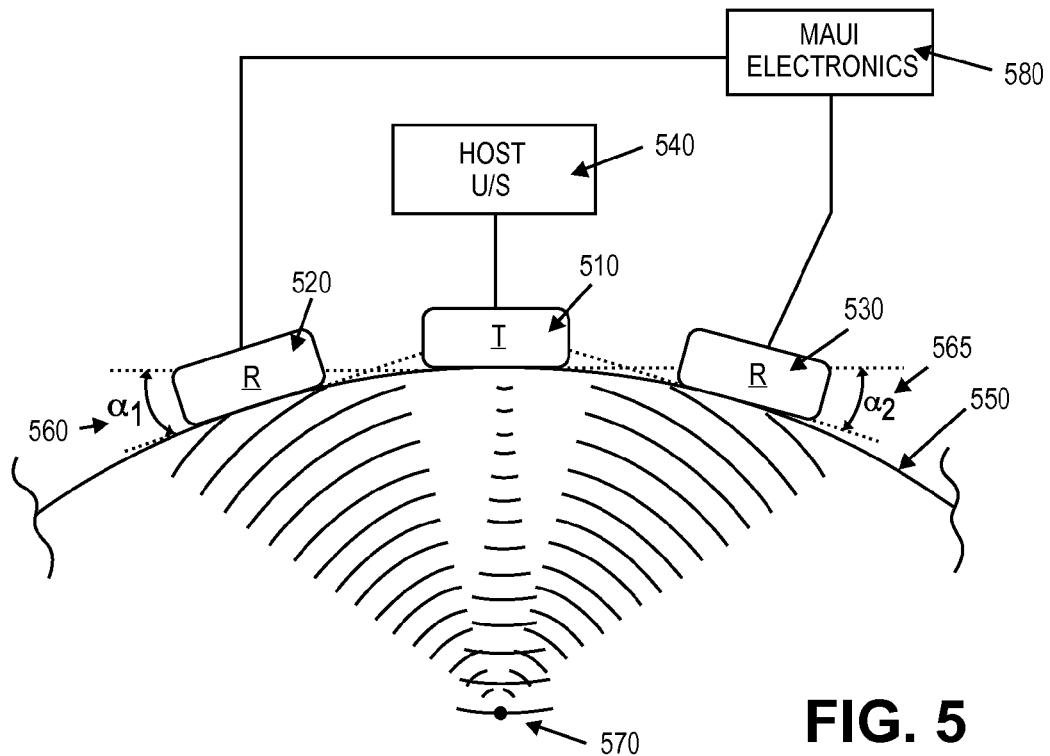
FIG. 5 is a block diagram of the transmit and receive functions where a three array Multiple Aperture Ultrasound Transducer and the associated MAUI electronics are used in conjunction with a host ultrasound machine. In this embodiment, the center probe is used for transmit only and mimics the normal operation of the host transmit probe.
Figure 5A:
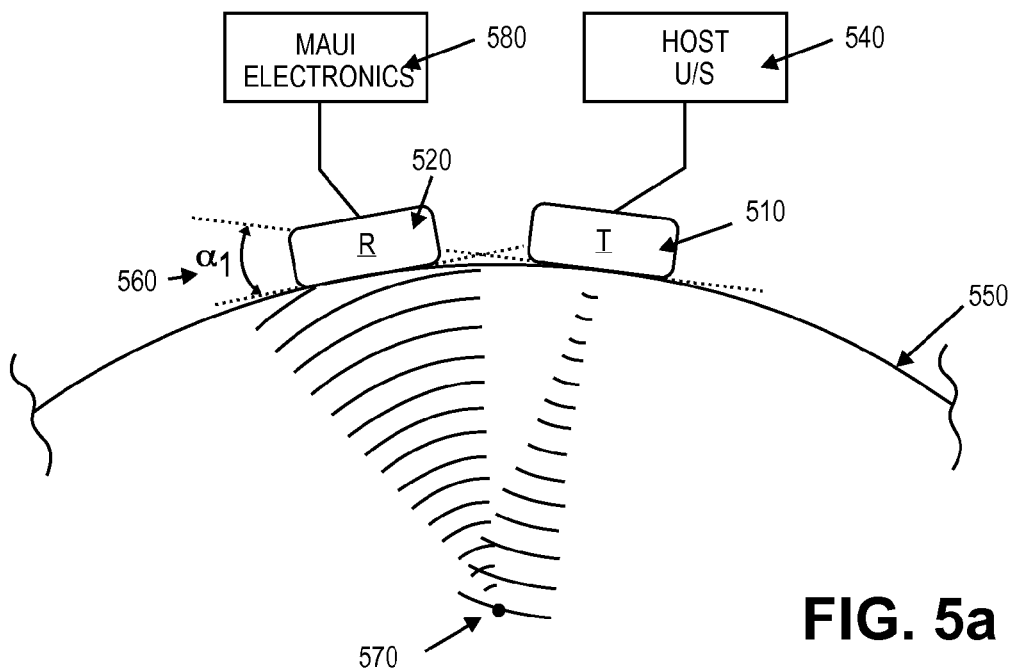
FIG. 5a is a block diagram of the transmit and receive functions where a two array Multiple Aperture Ultrasound Transducer and the associated MAUI electronics are used as an add-on to a host ultrasound machine, primarily for cardiac applications, with an add-on instrument. In this case, one probe is used for transmit only and mimics the normal operation of the host transmit probe, while the other probe operates only as a receiver.

In FIG. 5, the entire probe, when assembled together, is used as an add-on device. It is connected to both an add-on instrument or MAUI Electronics 580 and to any host ultrasound system 540. The center array 510 can be used for transmit only. The outrigger arrays 520 and 530 can be used for receive only and are illustrated here on top of the skin line 550. Reflected energy off of scatterer 570 can therefore only be received by the outrigger arrays 520 and 530. The angulation of the outboard arrays 520 and 530 are illustrated as angles $\alpha_1$ 560 or $\alpha_2$ 565. These angles can be varied to achieve optimum beamforming for different depths or fields of view. $\alpha_1$ and $\alpha_2$ are often the same for outboard arrays, however, there is no requirement to do so. The MAUI Electronics can analyze the angles and accommodate unsymmetrical configurations. FIG. 5a demonstrates the right transducer 510 being used to transmit, and the other transducer 520 is being used to receive.

Figure 6:
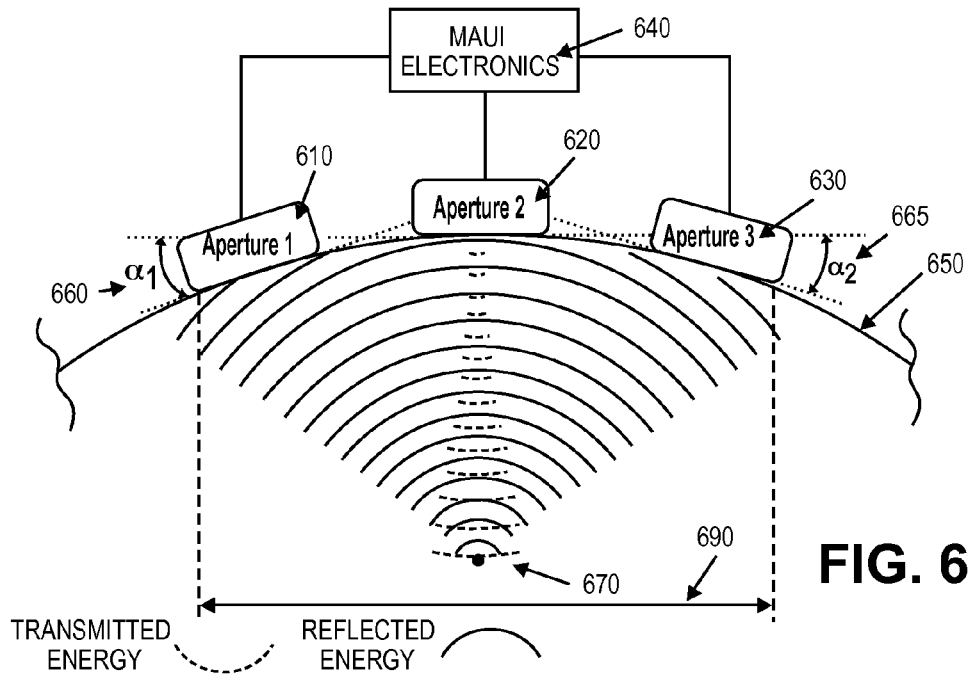
FIG. 6 is a block diagram of the transmit and receive functions where a Multiple Aperture Ultrasound Transducer is used in conjunction with only a Multiple Aperture Ultrasonic Imaging (MAUI) device. The stand-alone MAUI electronics control all elements on all apertures. Any element may be used as a transmitter or omni-receiver, or grouped into transmit and receive full apertures or even sub-arrays. In this figure the insonification emanates from the central aperture, aperture 2 of 3 apertures.

FIG. 6 is much like FIG. 5, except the Multiple Aperture Ultrasound Imaging System (MAUI Electronics) 640 used with the probe is a stand-alone system with its own onboard transmitter (i.e., no host ultrasound system is used). This system may use any element on any transducer 610, 620, or 630 for transmit or receive. The angulation of the outboard arrays 610 and 630 is illustrated as angle $\alpha$ 660. This angle can be varied to achieve optimum beamforming for different depths or fields of view. The angle is often the same for outboard arrays; however, there is no requirement to do so. The MAUI Electronics will analyze the angle and accommodate unsymmetrical configurations.

Figure 6A:
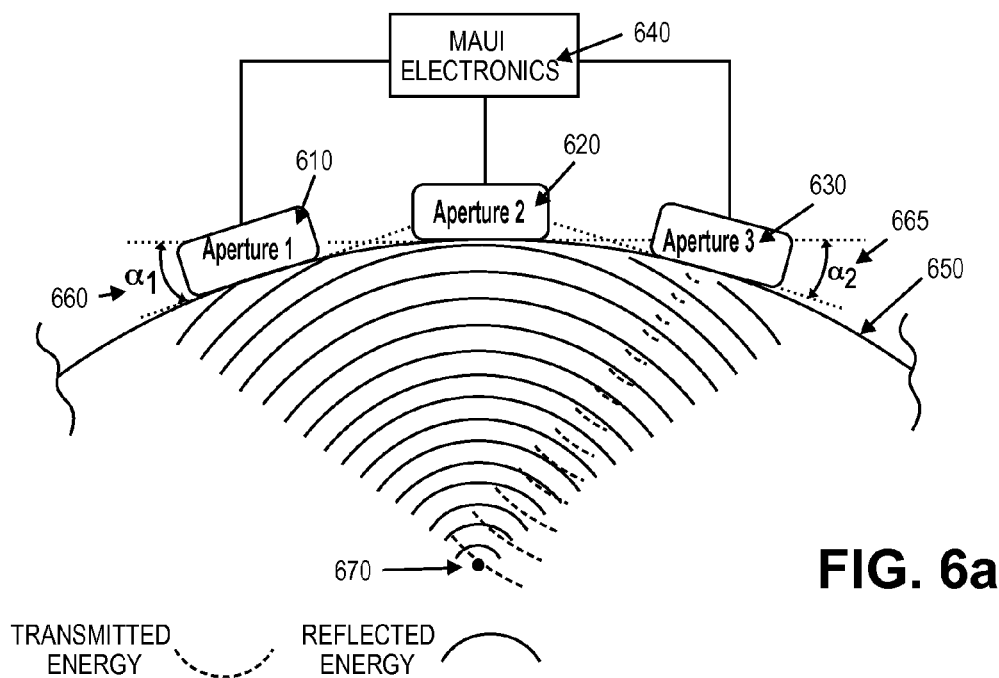
FIG. 6a depicts the insonification emanating from other than center aperture, in this figure Aperture 3 of 3.
Figure 6B:
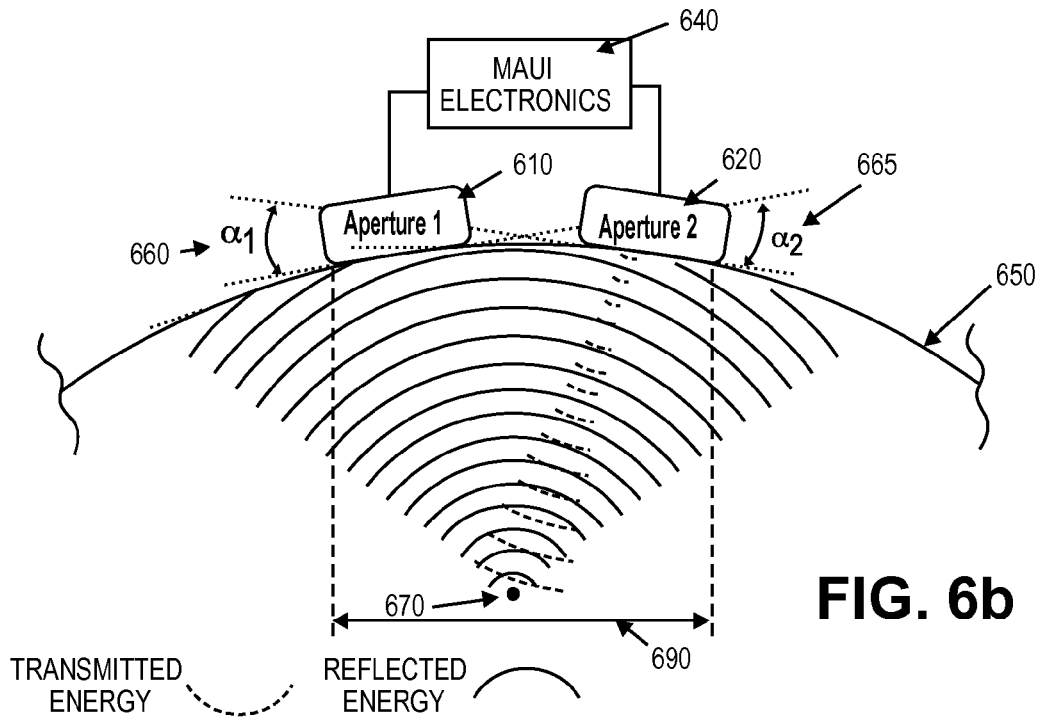
FIG. 6b is an illustration of two apertures being used a Multiple Aperture Ultrasound Transducer is used in conjunction with only a Multiple Aperture Ultrasonic Imaging (MAUI) device. In this figure the insonification emanates from aperture 2 of 2.

In this illustration, transmitted energy is coming from an element or small group of elements in Aperture 2 620 and reflected off of scatterer 670 to all other elements in all the apertures. Therefore, the total width 690 of the received energy is extends from the outermost element of Aperture 1 610 to the outmost element of Aperture 2 630. FIG. 6a shows the right array 610 transmitting, and all three arrays 610, 620 and 630 receiving. FIG. 6b shows elements on the left array 610 transmitting, and elements on the right array 620 receiving. Using one transducer for transmit only has advantages with regard to a lack of distortion due to variation in fat layer. In a standalone system, transmit and/or receive elements can be mixed in both or all three apertures.

Figure 6C:
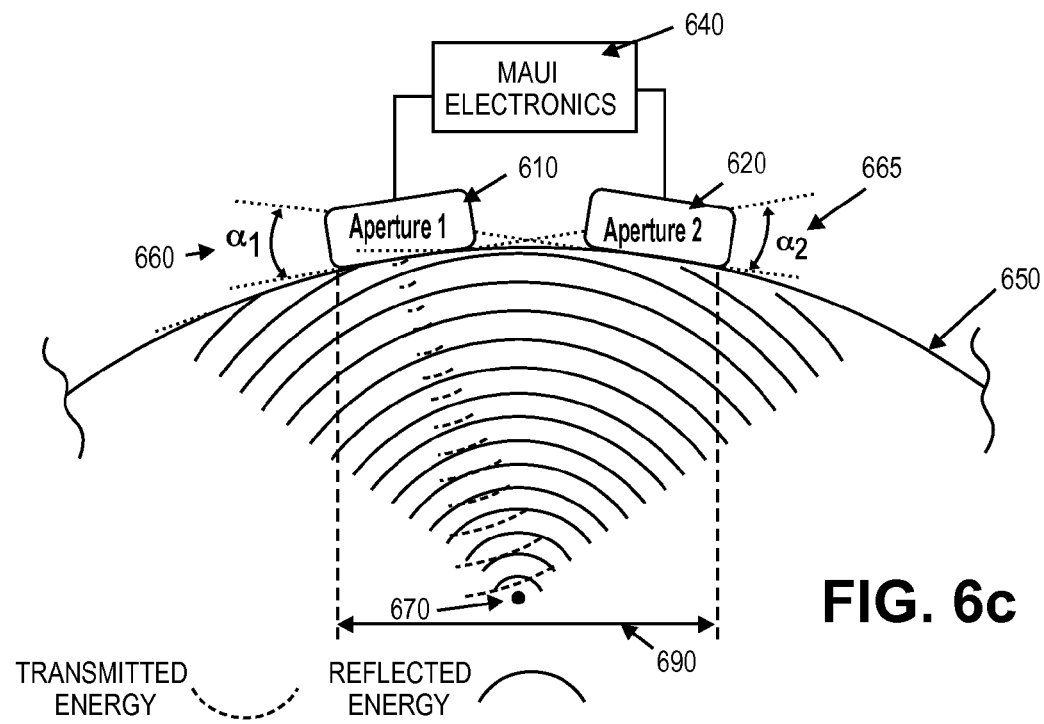
FIG. 6c is an illustration of two apertures being used a Multiple Aperture Ultrasound Transducer is used in conjunction with only a Multiple Aperture Ultrasonic Imaging (MAUI) device. In this figure the insonification emanates from aperture 1 of 2.

FIG. 6b is much like FIG. 5a, except the Multiple Aperture Ultrasound Imaging System (MAUI Electronics) 640 used with the probe is a stand-alone system with its own o-board transmitter. This system may use any element on any array 610 or 620 for transmit or receive as is shown in FIG. 6c. As shown in either FIG. 6b or FIG. 6c, a transmitting array provides angle off from the target that adds to the collective aperture width 690 the same way two receive only transducers would contribute.

Figure 7A:
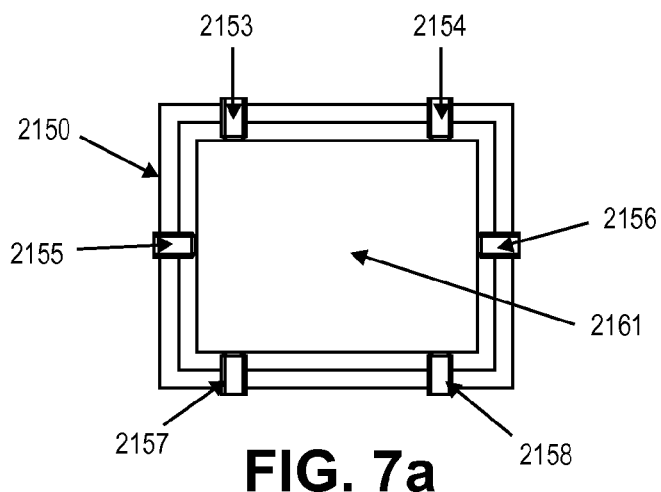
FIG. 7a is a top view of the precision array carrier with six adjustment screws and an array installed.
Figure 7B:
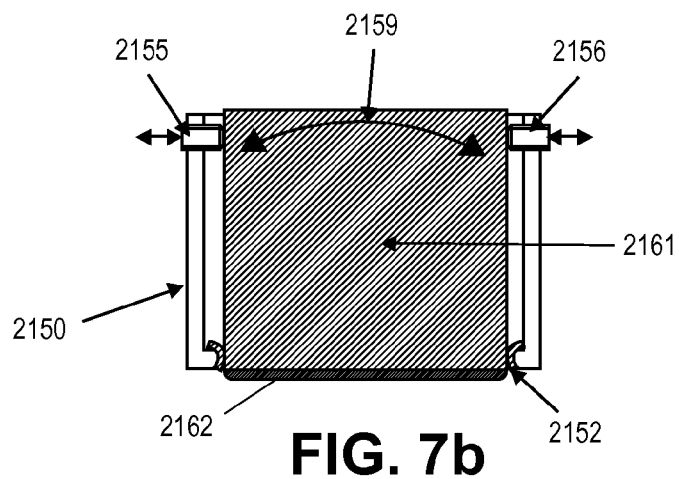
FIG. 7b is a side view showing the longitudinal axis adjustment of an array in the precision array carrier being supported by the array-centering gasket.
Figure 7C:
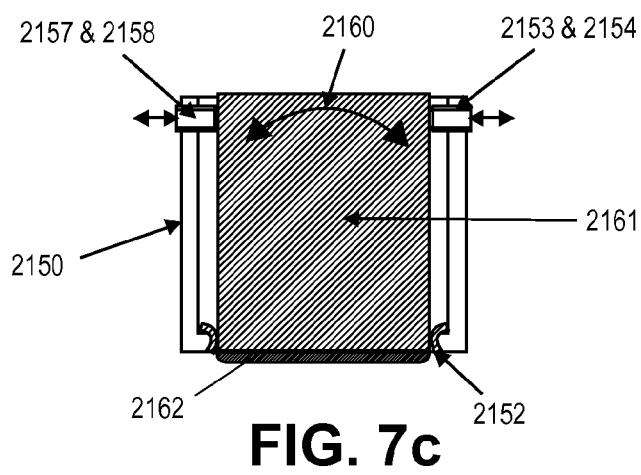
FIG. 7c is an end view showing the transverse axis adjustment of the array in the precision array carrier being supported by the array-centering gasket.

Embodiments described herein include a precision carrier for the proper alignment of a universal multiple aperture ultrasound transducer. Referring now to FIGS. 7a-7c, transducer array 2161 can be already "potted" in its own fixture 2161 with lens 2162 intact. Potting procedures are conventional methods to secure the transducer array to its lens and to the case. Flex circuitry, cabling, and attachment to the larger multiple aperture ultrasound transducer fixture can take place after the potting procedure is complete. A benefit of the invention is that it does not require the same transducers to be utilized during the alignment. Different transducers with different "pots" can be utilized in any location of the alignment fixture thanks to the flexibility of the alignment carrier.

Figure 8A:
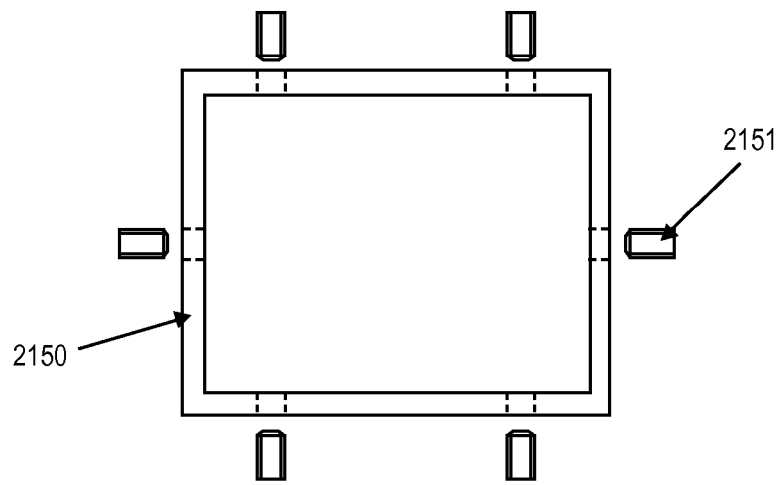
FIG. 8a is a top view of the precision array carrier.
Figure 8B:
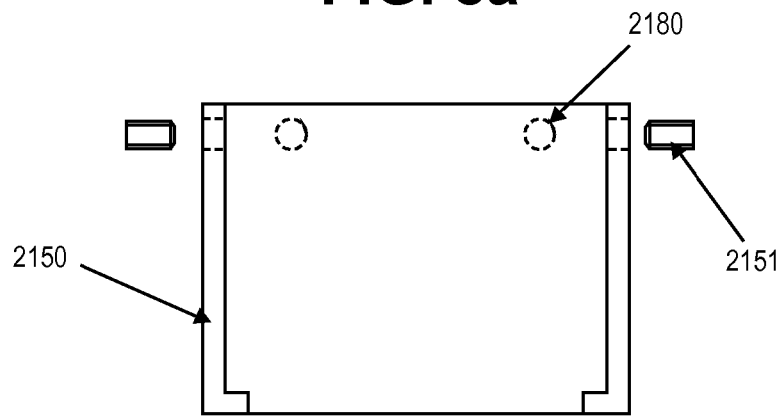
FIG. 8b is a side (longitudinal) view of the precision array carrier.
Figure 8C:
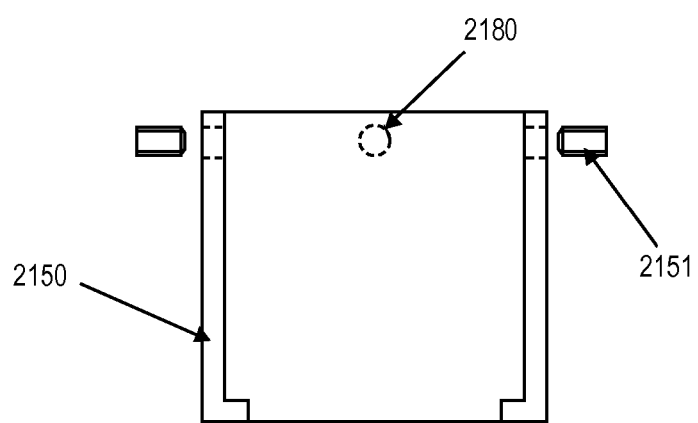
FIG. 8c is an end (lateral) view of the precision array carrier.

FIGS. 8a-8c provide views of the basic structure and features of embodiments of a precision carrier 2150 for a multiple aperture ultrasound transducer array. FIG. 8a shows a top view of a precision array carrier 2150 with six positioning screws 2151. FIG. 8b shows a side view of a precision array carrier 2150 having two threaded screw holes 2180 on each side. When positioning screws 2151 are inserted into threaded screw holes (e.g., screw holes 2155 and 2156 in FIG. 7b), adjustments may be made to employ longitudinal corrections 2159 to the "seated" array. FIG. 8c shows a side view of a precision carrier 2150 with threaded screw holes 2180 located on each end. When positioning screws are inserted into these threaded screw holes, adjustments may be made to employ lateral corrections 2160 to the "seated" array (as illustrated in FIG. 7c).

Figure 9A:
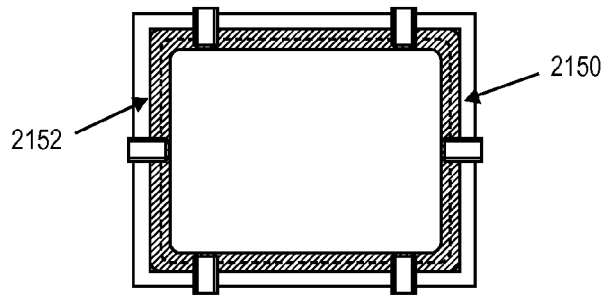
FIG. 9a is a top view of the precision array carrier with a centering gasket in place.
Figure 9B:
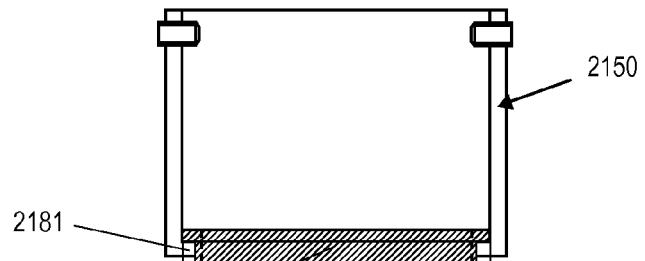
FIG. 9b is a side view (longitudinal) of the precision array carrier with a centering gasket in place.
Figure 9C:
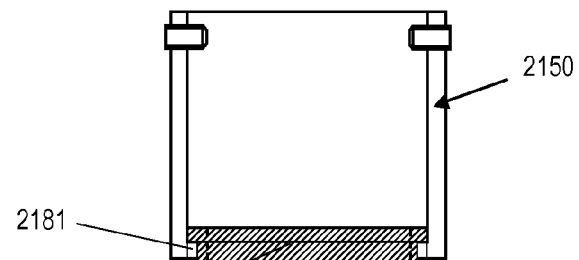
FIG. 9c is an end view (lateral) the precision array carrier with a centering gasket in place.
Figure 9D:
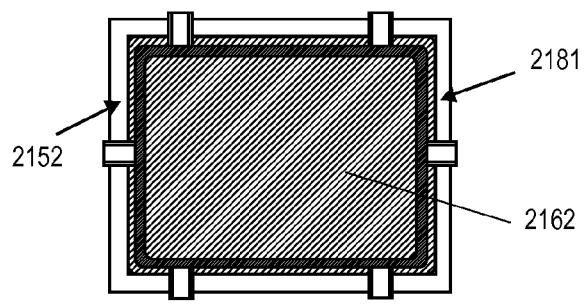
FIG. 9d is a bottom view of the precision array carrier with a centering gasket in place.

FIGS. 9a-9d show a precision array carrier 2150 with an array-centering gasket 2152 installed. FIG. 9a is a top view of the precision carrier 2150, with an array-centering gasket 2152 placed at the bottom of the carrier where the lens 2162 located in the center. FIGS. 9b-9d show side, end, and bottom views of the carrier, respectively. The array centering gasket 2152 on the carrier's L shaped shoulder 2181 as illustrated in FIG. 7b. In FIG. 9b the gasket 2152 extends the entire length of the carrier over the L shaped shoulder 2181. The gasket 2152 extends around the corners of the L shaped shoulder 2181 to cover the ends of the carrier as it illustrated in FIG. 9c. The gasket provides the array translational centering and a pivot point for positioning adjustments during operation without interfering with the integrity of the lens 2162. FIG. 9d provides a view of the lens 2162, the bottom of the precision carrier array centering gasket 2152, and finally the L shaped shoulder 2181.

Referring back to FIGS. 7a-7c, which show top, end, and side views, respectively, of a precision array carrier 2150 with an array 2161 inserted therein. The array 2161 is supported end-to-end by positioning screws 2155 and 2156. The array can be supported from each side by positioning screws 2153, 2154, 2157, 2158 and from the bottom by the array centering gasket 2152. FIG. 7b shows the array 2161 in the precision array carrier 2150 being supported by array centering gasket 2152 and ready for longitudinal adjustment. Alternately tightening and loosening positioning screws 2155 and 2156 allows the array 2161 to be adjusted through arc 2159 to correct longitudinal axis errors. FIG. 7c shows the array 2161 in the precision array carrier 2150 supported by the array centering gasket 2152 ready for transverse alignment. Alternately adjusting positioning screw pairs 2157, 2158 and 2153, 2154 allow the array 2161 to be corrected for transverse axis errors.

Figure 10A:
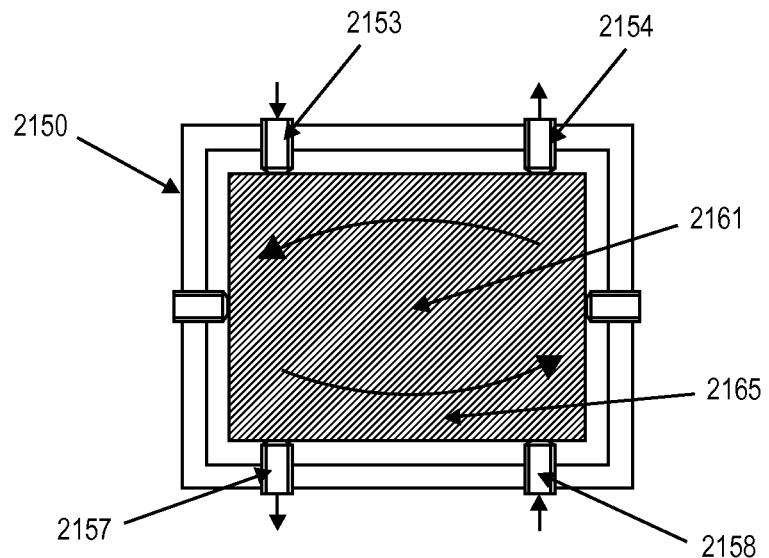
FIG. 10a is a top view of the array in the precision array carrier during a counter-clockwise rotational axis adjustment.
Figure 10B:
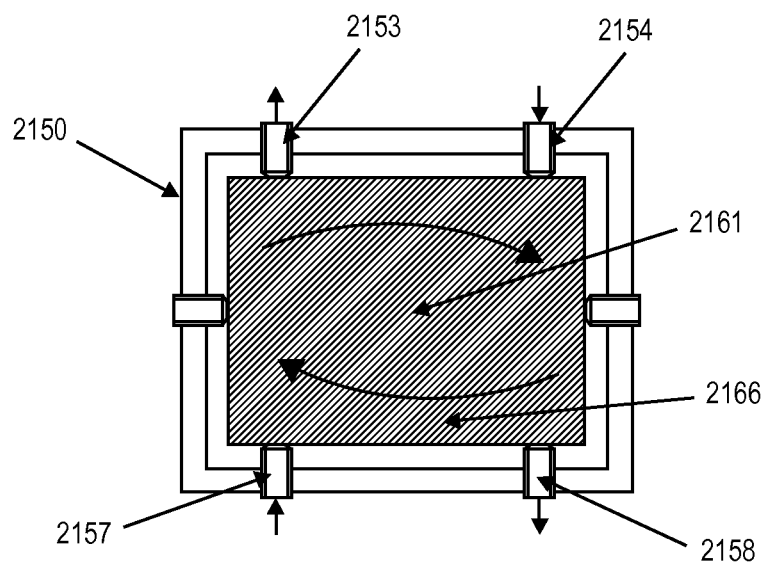
FIG. 10b is a top view of the array in the precision array carrier during a clockwise rotational axis adjustment.

FIGS. 10a and 10b show a top views of a precision array carrier 2150 with the array 2161 inserted. Arrows depict, respectively, counter-clockwise and clockwise rotational adjusting by way of selective screw adjustments. FIG. 10a shows a tightening of position screws 2153 and 2158 while loosening position screws 2154 and 2157 shifting the array 2161 in a counter-clockwise arc 2165 to correct rotational axis errors. FIG. 10b shows a tightening position of screws 2154 and 2157 while loosening position screws 2153 and 2158 to shift the array 2161 in a clockwise arc 2166 to correct rotational axis errors.

Figure 11:
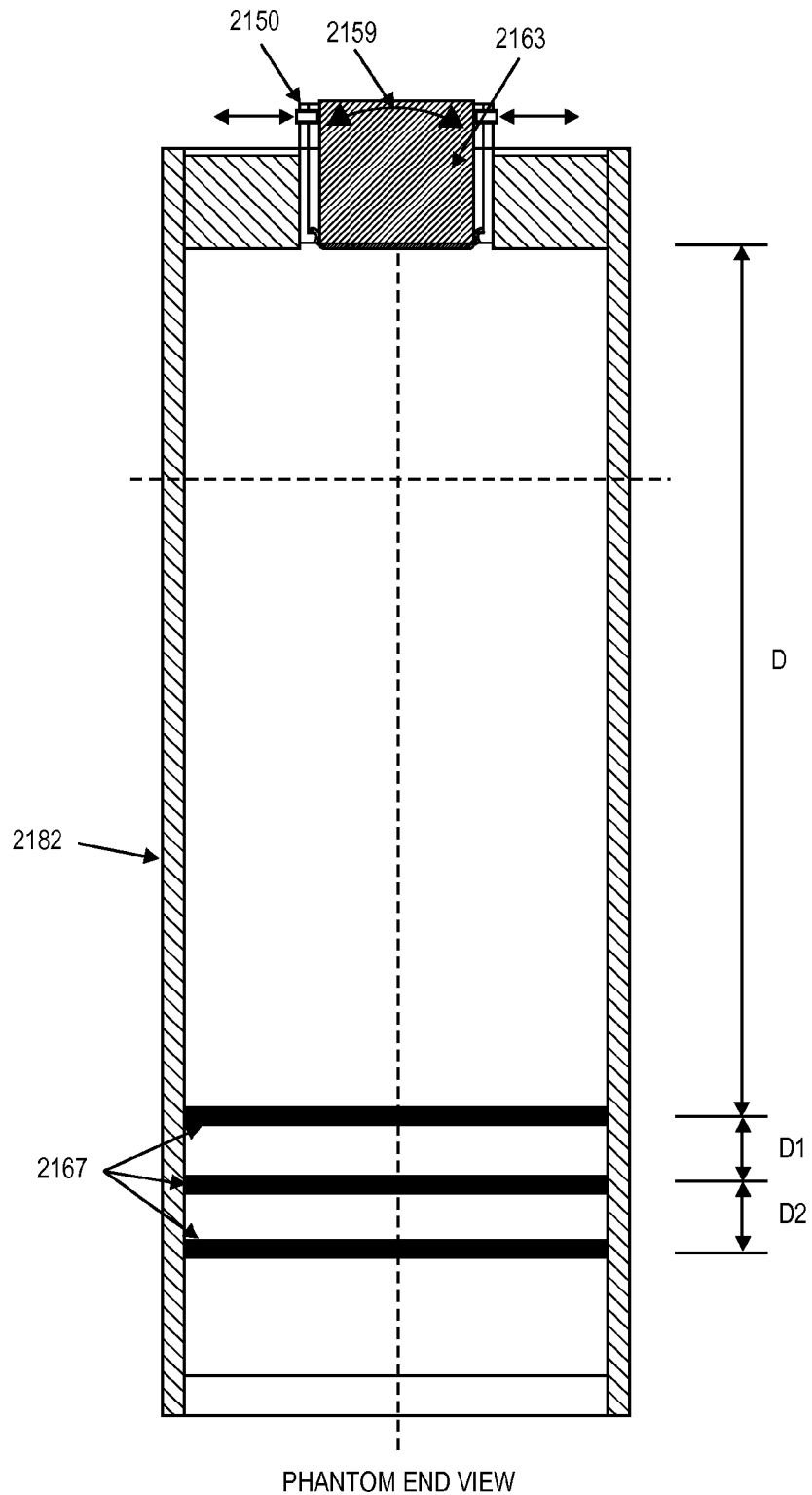
FIG. 11 shows an end view of a precision array carrier 2150 installed on a tissue equivalent phantom 2182 and ready to transmit and receive during alignment.

FIG. 11 shows an end view of a precision array carrier 2150 installed on a tissue equivalent phantom or test block 2182 and ready to transmit and receive during alignment. A 'phantom' is a structure filled with tissue equivalent material that has a speed of sound characteristics similar to that of human tissue with known voids and reflectors placed at known locations within the phantom. This end view of the phantom shows one embodiment including three targets 2167 in profile view. These targets can be echogenic, very reflective, or anechoic, void of reflection. The top target can be at a pre-determined depth D from the surface of the phantom and the face of array carrier 2150. The other targets can be spaced at distances D1 and D2 from the top target. In some embodiments, the pre-determined depth D can be 100 mm from the top target to the face of the array. The other targets can have D1 and D2 distances of 10 mm, for example. However, any range of depths for the targets 2167 can be used, depending on the desired application of the transducer arrays. The perpendicular targets 2167 serve to assist during the longitudinal adjustment of the array positioning. When correctly positioned, the three targets would be displayed as exactly perpendicular to the front of the array, and further, each target 2167 would be displayed equidistantly one a top the other.

Figure 12:
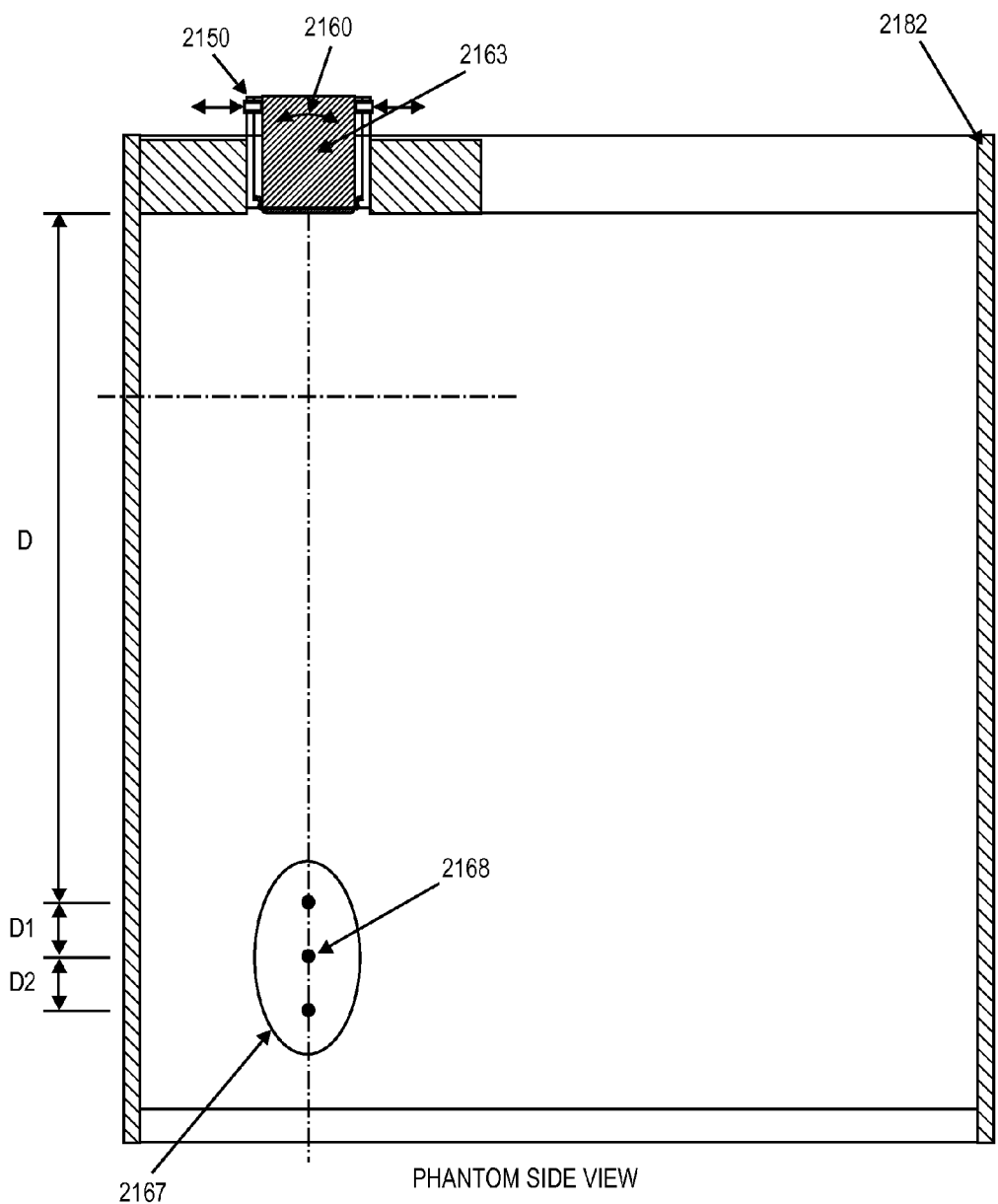
FIG. 12 shows a side view of the phantom 2182 with the ends of the targets 2167 visible.

FIG. 12 shows a side view of the phantom 2182 with the ends of the targets 2167 visible. Once transmitting and receiving, a lateral adjustment could be made to the array 2163 in the carrier 2150. The correct alignment is for achieved when all targets are visible above and below the center target 2168.

Figure 13A:
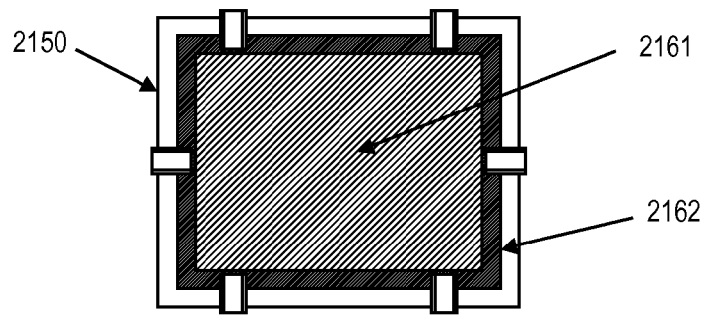
FIG. 13a is a top view of a carrier assembly with arrays installed (to become a precision carrier array assembly) and aligned within a precision transducer receptacle and stabilized with an acoustic damping material.
Figure 13B:
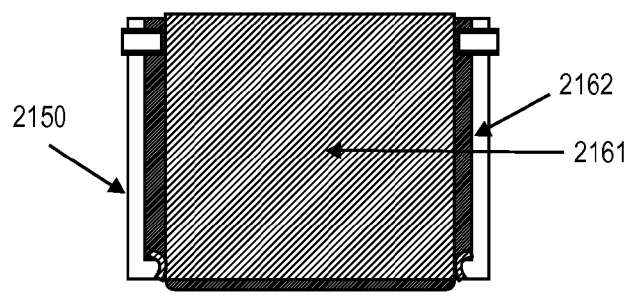
FIG. 13b is a side view of a precision array carrier with arrays installed (to become a precision carrier array assembly) and aligned within a precision transducer receptacle and stabilized with an acoustic damping material.
Figure 13C:
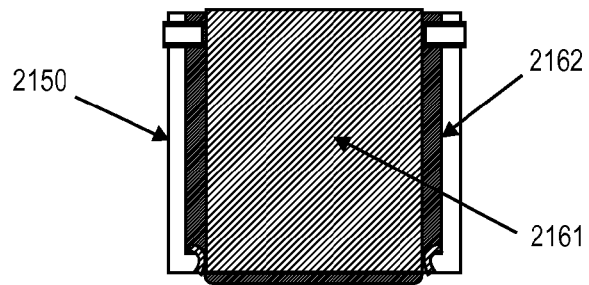
FIG. 13c is an end view of a precision carrier array with arrays installed (to become a precision carrier array assembly) and aligned within a precision transducer receptacle and stabilized with an acoustic damping material.

FIGS. 13*a*-13*c* show a precision array carrier 2150 with an array 2161 inserted and aligned, in top, side, and end views, respectively. At this stage an acoustic damping material 2162 can be poured into the gap between the array and the carrier to stabilize the position of arrays 2161. FIG. 13*b* is a side view of the precision array carrier 2150 showing the gap between the array 2161 and the precision array carrier 2150 filled with acoustic damping material 2162. FIG. 13*c* shows the gap between the array 2161 and the precision array carrier 2150 filled with acoustic damping material 2162.

Figure 14A:
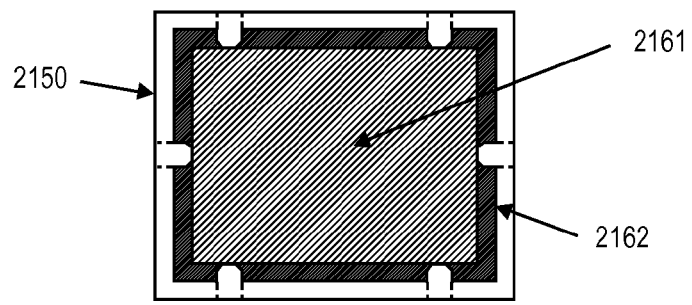
FIG. 14a is a top view of a precision carrier array with arrays installed and aligned within a precision transducer head receptacle, the acoustic damping material has set and alignment screws have been removed.
Figure 14B:
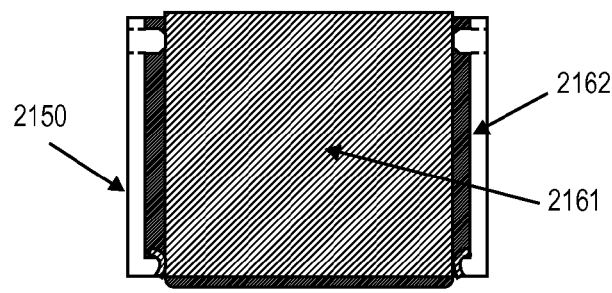
FIG. 14b is a side view of a precision carrier array assembly with arrays installed and aligned within a precision transducer head receptacle, the acoustic damping material has set and alignment screws have been removed.
Figure 14C:
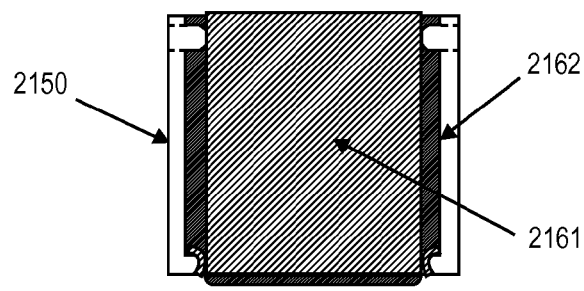
FIG. 14c is an end view of a precision carrier array with arrays installed and aligned within a precision transducer head receptacle, the acoustic damping material has set and alignment screws have been removed.

FIGS. 14*a*-14*c* show the precision array carrier 2150 with the array 2161 inserted and aligned in top, side, and end views, respectively. The acoustic damping material 2162 has cured and the six alignment screws have been removed. FIG. 14*b* is a side view of the precision array carrier 2150 with the array 2161 inserted, aligned, the acoustic damping material 2162 cured and the position alignment screws removed: At this point, the precision array carrier 2150 with its captured array becomes a precision carrier array assembly 2163.

Figure 15:
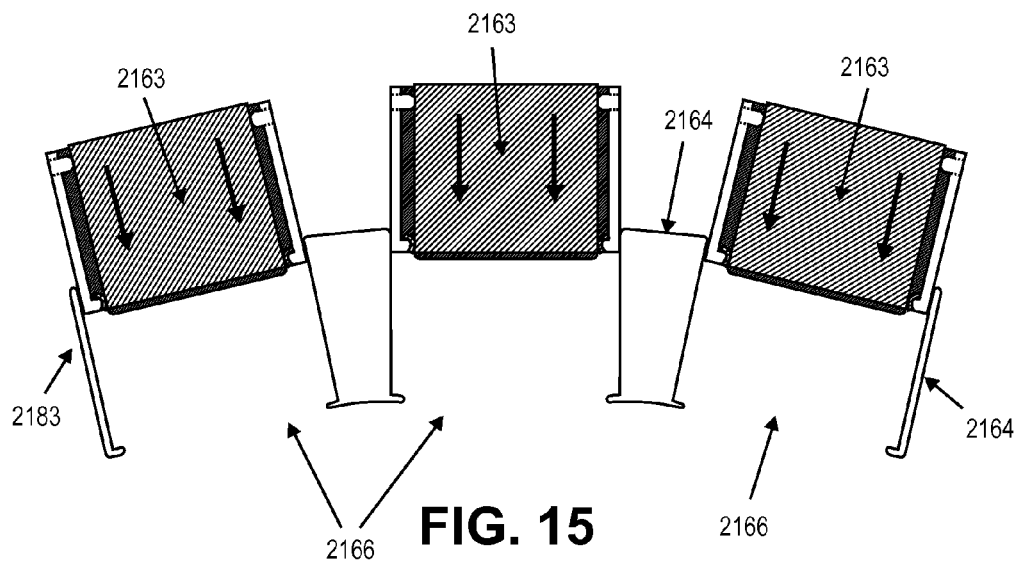
FIG. 15 shows a precision transducer receptacle or nose piece and three precision carrier array assemblies seated atop the transducer guides.

FIG. 15 shows a multi-aperture ultrasound probe assembly 2183 constructed with precision transducer receptacles surrounded by structural supports 2164. The structural supports 2164 can be constructed out of many hard materials (e.g., metals or plastics) and usually are built into a larger structure such as the probe 2200 in FIG. 22. In FIG. 15, the three precision carrier array assemblies 2163 are inserted into the precision transducer receptacles 2166.

Figure 16:
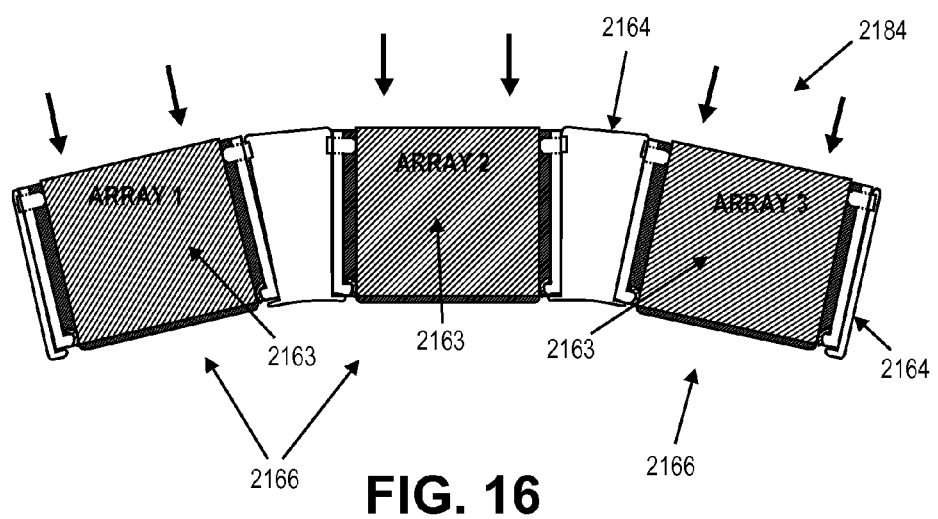
FIG. 16 shows the precision transducer receptacle or nose piece and three precision carrier array assemblies as in FIG. 16, and an ultrasound transducer array seated in each transducer guide of the nose piece.

FIG. 16 shows the multi-aperture probe assembly 2183 having precision transducer receptacles 2166 with the precision array assemblies 2163 each locked into the receptacles, thus completing the construction of the multi-aperture ultrasound probe 2184 having three transducer arrays.

Figure 22:
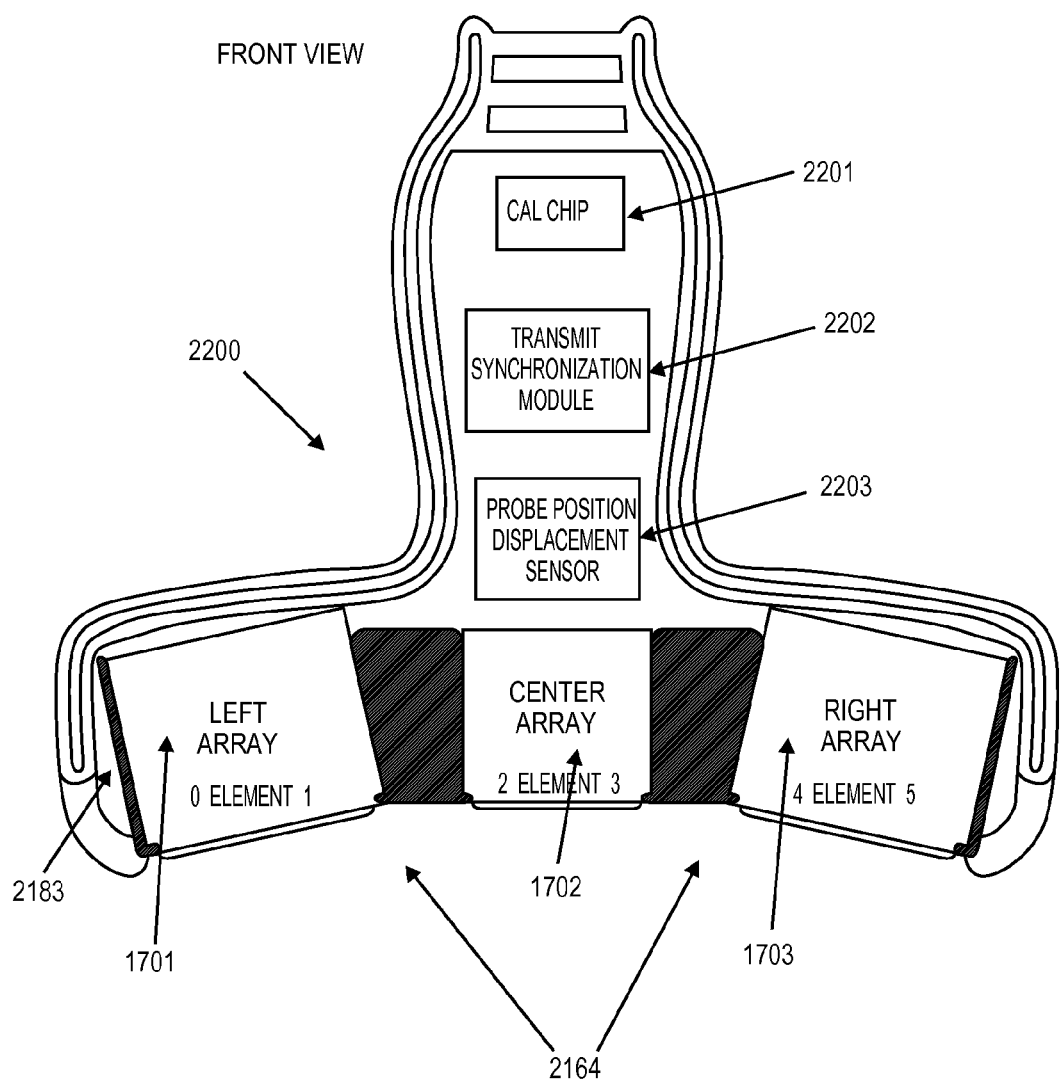
FIG. 22 illustrates a nose piece containing three separate arrays after it is installed into a Multiple Aperture Transducer. This figure includes the transducer specific calibration chip, the transmit synchronization module and probe position displacement sensor.

FIG. 22 shows a completed probe 2200 with arrays 1701, 1702, and 1703 fitted in array receptacles and ready for submission to the calibration cycle.

Alternative apparatus and methods for constructing and aligning multi-aperture ultrasound probes will now be discussed. As described above, variations in the ultrasound beam displacement or rotation of both the insonifying and receiving probes about the x, y and z axes must be detected and corrected. A MAUI alignment fixture for aligning a multi-aperture probe uses one or more precision angular alignment controls, precision stage assemblies that provide for the adjustment, in 6 degrees of freedom of the each array under test.

One of the great practical difficulties in making multi-aperture imaging systems, as outlined above, is the requirement to precisely align the elements of the multiple arrays. It is well recognized that by increasing the effective aperture of a probe system by including more than one probe head and using the elements of all of the probes to render an image, the lateral resolution of the image can be greatly improved. In order to render an image, the relative positions of all of the elements must be known precisely. Optionally, if the probe system has position and rotation adjustments, a display is provided to position all of the elements to be in the same plane of scan and to transmit or receive in the same plane of scan.

Figure 17:
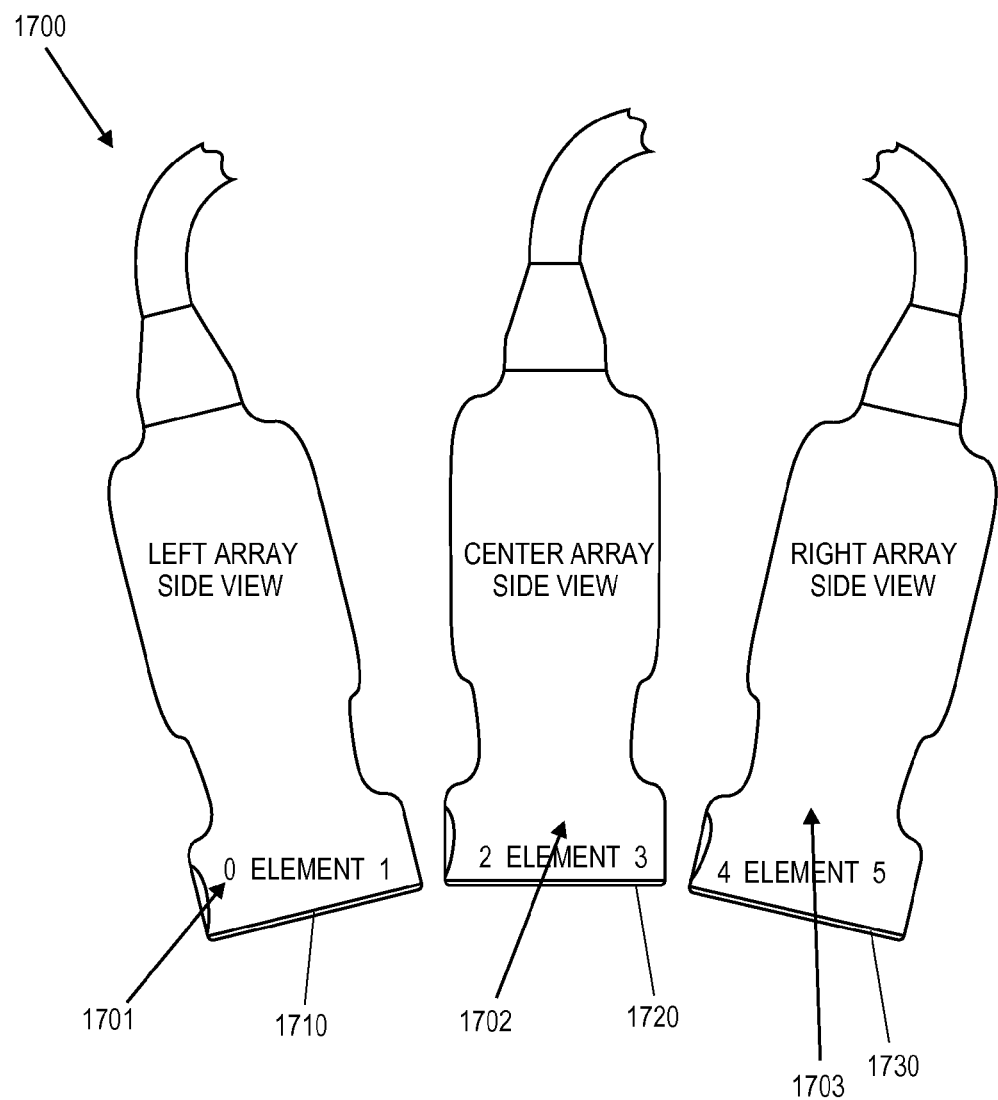
FIG. 17 is a drawing using three independent probes and their installed arrays or transducers. This illustration represents the positional nomenclature and array element numbering conventions.

FIG. 17 shows a probe system 1700 comprising three probes 1701, 1702, and 1703 working together as a multi-aperture transducer though not assembled in a single shell. This is not a standard embodiment of a multiple aperture transducer, but serves here to aid in describing arrays alignment. A multi-aperture transducer can comprise of any number of arrays 1710, 1720, 1730 (two or more), or even individual elements. For practical reasons, arrays in probes can easily be manufactured with a large number of elements and element spacing within a head can be well controlled. If one can precisely position the end elements of each probe, it is possible to imply the positions of the other elements. Therefore, a fixture will be described which finds the positions of the elements. This apparatus could determine the exact location of independent elements either inside or outside of an array; however, because arrays are typically constructed in a linear format, the embodiment discussed here only identifies the end elements.

In FIG. 17 these end elements are designated as element numbers 0 through 5, where 0 and 1 are the end elements of array 1710, 2 and 3 are the end elements of arrays 1720 and 4 and 5 are the end elements of array 1730. Any of the intermediate elements could be located in the same way as will be described.

Figure 18A:
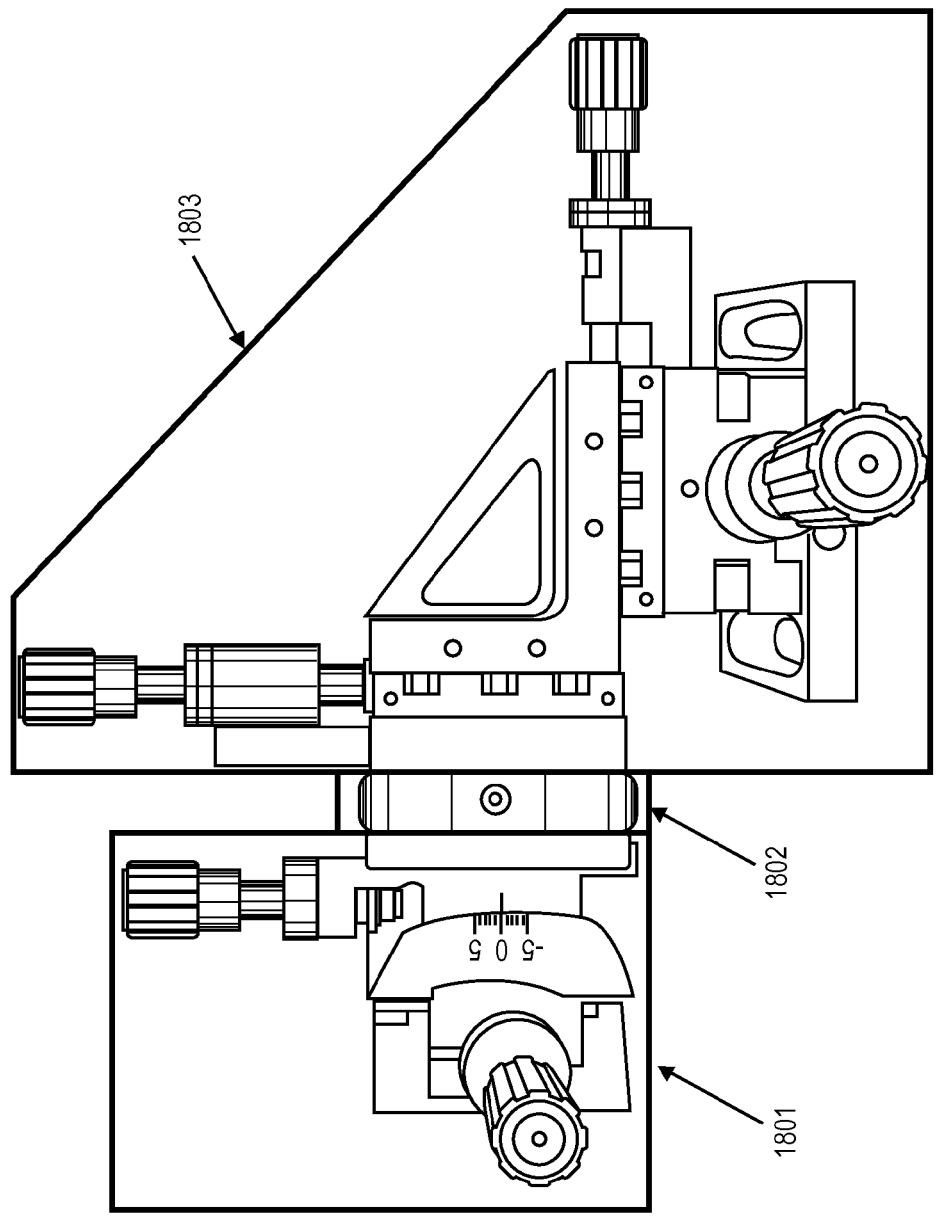
FIG. 18a shows the Precision Stage Assembly and sections that control movement in three different axes.
Figure 18B:
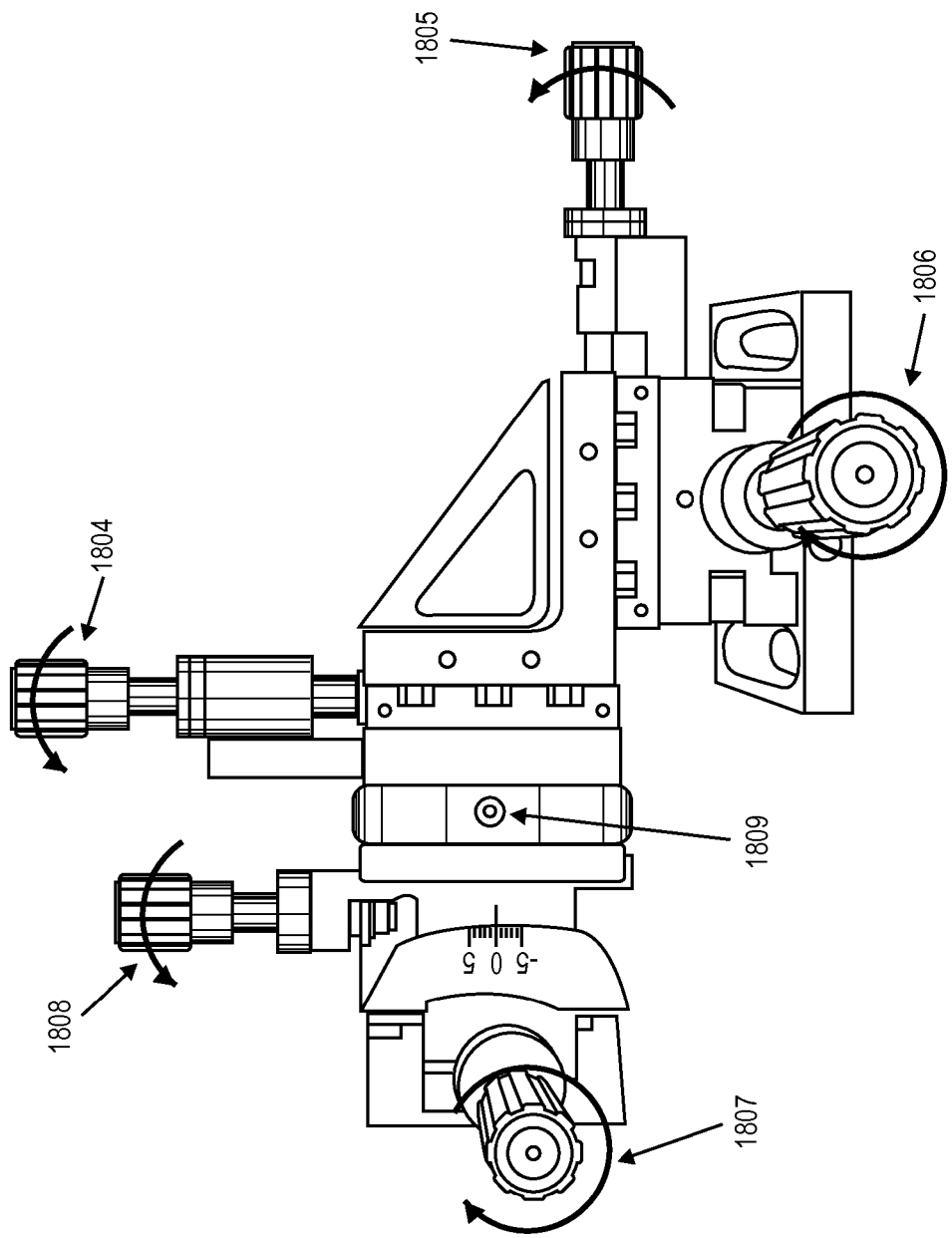
FIG. 18b shows the controls for the Precision Stage Assembly.

A precision alignment stage assembly is shown in FIG. 18*a*. The far left area of the assembly 1801 allows for the mechanical connection of a single probe, such as 1701 from FIG. 17. The precision alignment stage assembly has three separate mechanisms 1801, 1802 and 1803 that control the position of the attached array in x, y and z axes. Several alignment stage assemblies can be used in concert so that multiple probe arrays can be manipulated independently. FIG. 18*b* allows the operator to manipulate an array in any axis by using controls 1805, 1806, 1807, 1808, and bearing 1809. Precision screws 1804, 1805, 1806, 1807, and 1808 can be adjusted, and bearing 1809 can be rotated to affect one or more axes for the array during the alignment process.

Figure 25:
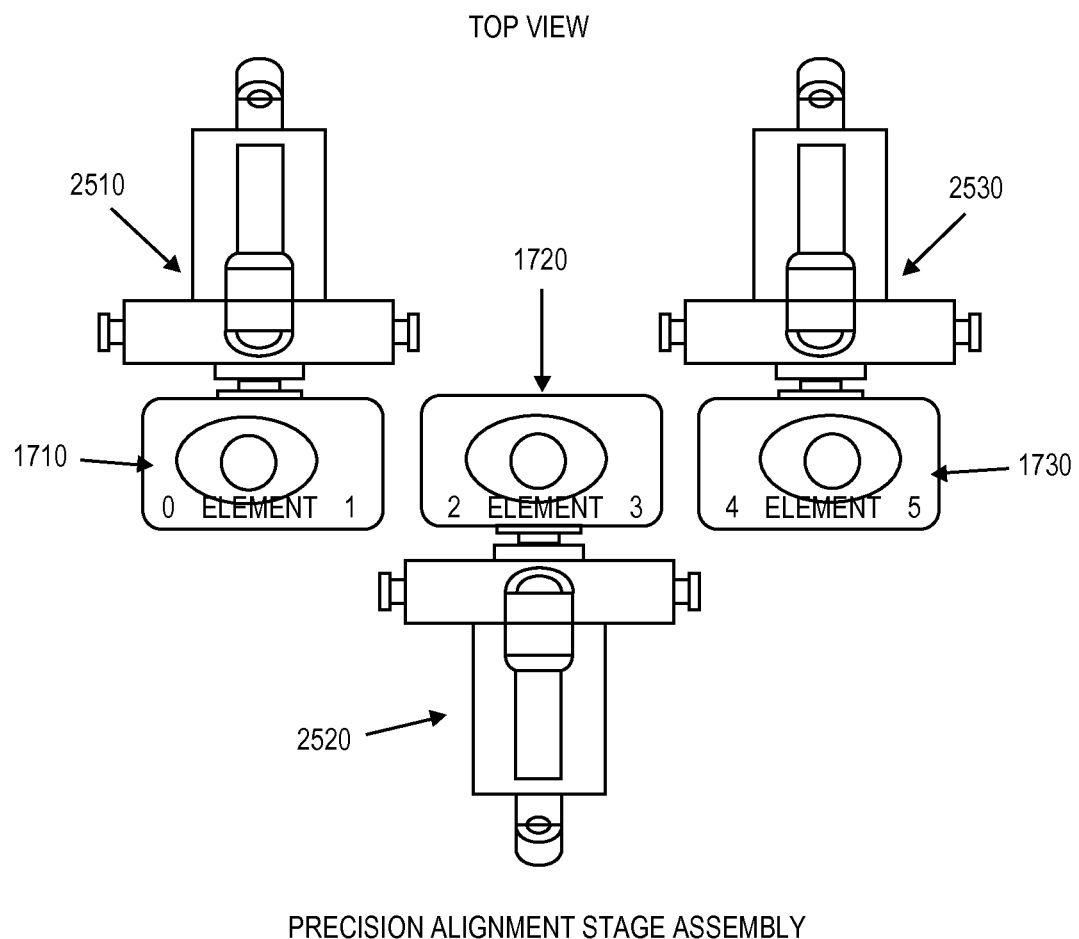
FIG. 25 is a representation using three arrays and three precision alignment stage assemblies showing their physical placement during testing.

FIG. 25 shows the arrays 1710, 1720 and 1730 attached in line to precision alignment stages 2510, 2520 and 2530. With the arrays set in place, they can now transmit to common points of interest and compare their points of impact with the other arrays.

Figure 20:
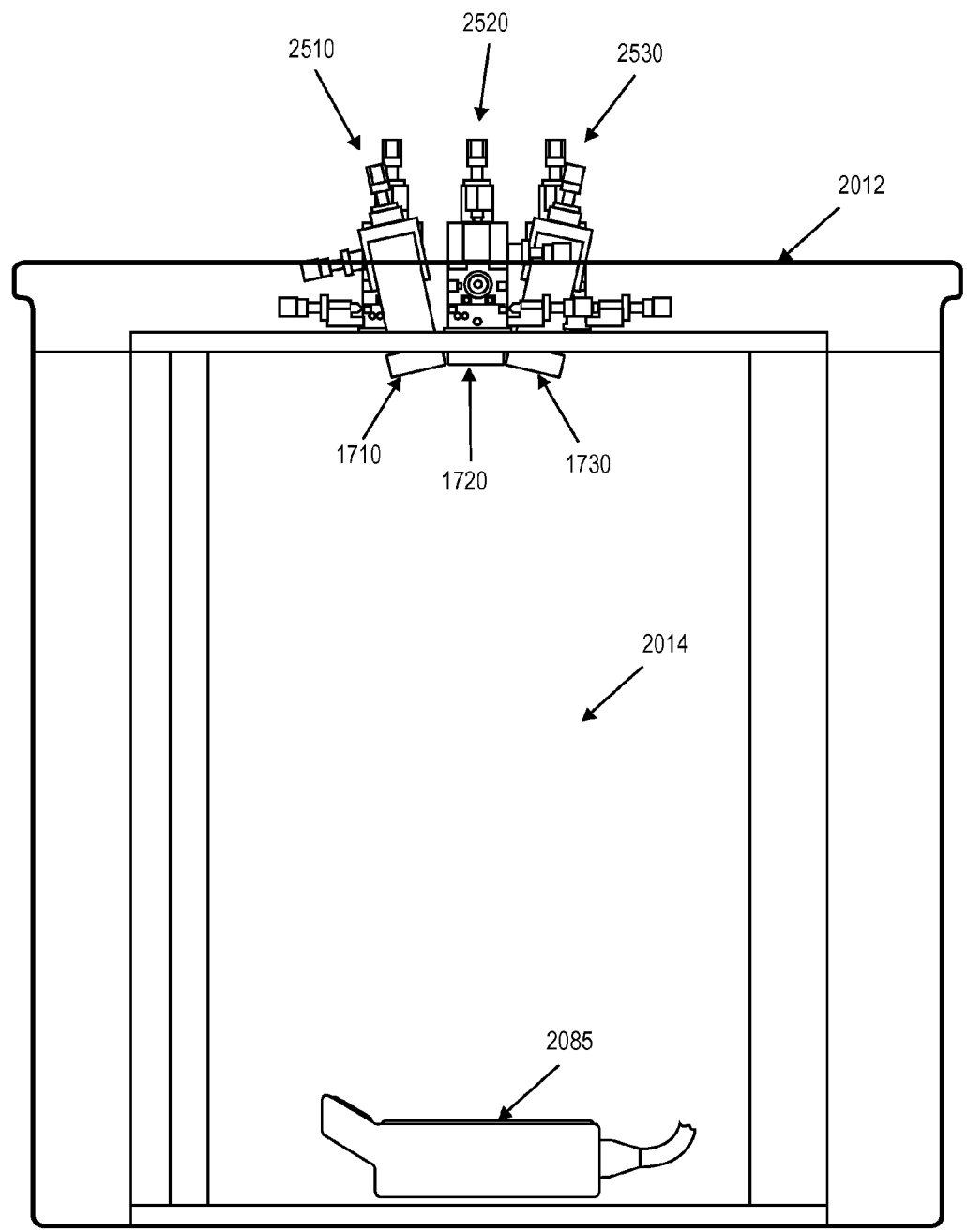
FIG. 20 is a representation of probes attached to the precision stage assemblies on top of a fluid filled tank, and well above the hydrophone assembly.

FIG. 20 illustrates probes 1701, 1702 and 1703 from FIG. 17 now attached to alignment stage assemblies above a tank or test block 2012. The tank can be filled with any liquid, fluid, gel, solid, or other medium 2014 that is desirable for manufacture and safety considerations, as long as the speed of sound for the fluid is known. The tank can include a mounting location for the alignment stage assemblies. In some embodiments, as shown in FIG. 20, multiple alignment stage assemblies holding transducer elements can be mounted on the test block. From this position, it is possible to transmit ultrasonic pulses from the elements of any of the arrays to be received by ultrasonic sensor or hydrophones 2085 at the other end of the tank 2012.

Figure 19A:
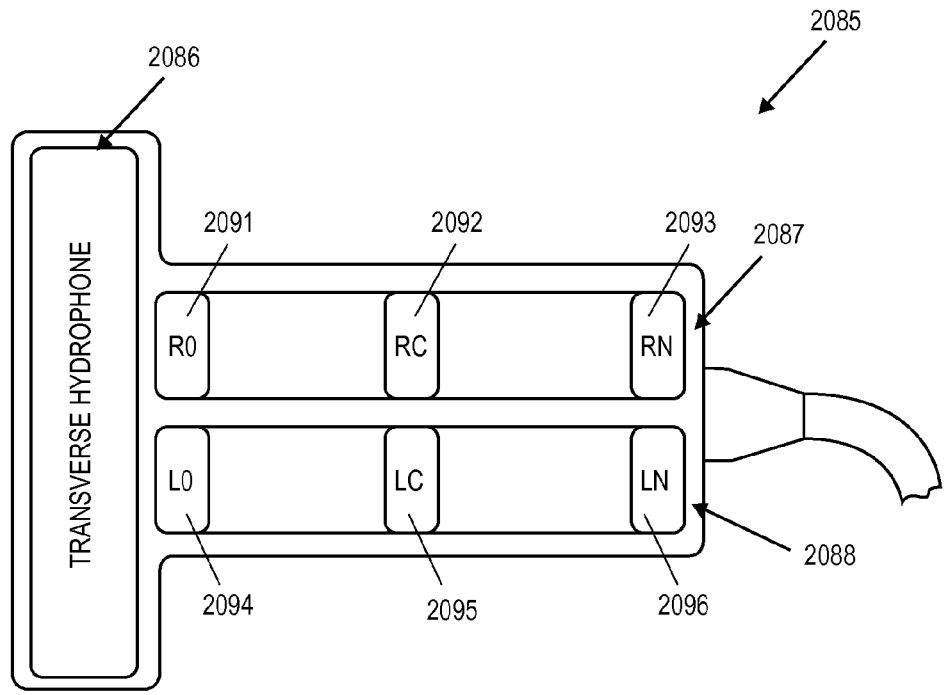
FIG. 19a depicts is an enclosure containing Right and Left Axial Hydrophones and a Transverse Hydrophone.
Figure 19B:
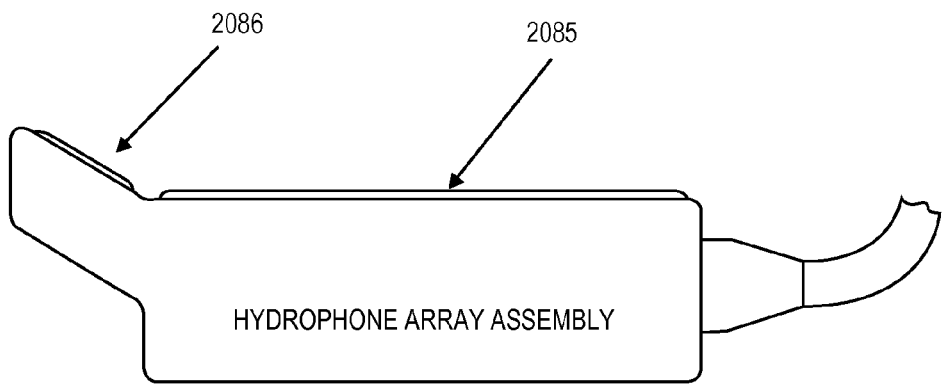
FIG. 19b depicts the dual Axial Hydrophones from the side and illustrates the angular orientation of the Transverse Hydrophone.

Referring now to FIGS. 19a-19b, a multi-axis ultrasonic sensor or hydrophone 2085 may be used to detect the X, Y and Z positions of each element of a single array or multiple arrays under test. The multi-axis hydrophone 2085 can include a transverse hydrophone 2086, and right and left hydrophones 2087 and 2088. The common targets for the probes 1701, 1702 and 1703 to shoot at are elements 2091, 2092 and 2093 on the right hydrophone 2087. On the left hydrophone 2088, elements 2094, 2095, and 2096 are the targets.

The basic technique for aligning and calibrating a multiple aperture probe can now be addressed referring to FIGS. 19a, 19b and 20. The probe can be attached to a signal generator configured to excite any of the transducer elements to transmit ultrasonic pulses. An ultrasonic signal is transmitted which exhibits good autocorrelation properties (e.g., a long frequency sweep, or 'chirp' waveform, a short (wideband) pulse, a spread spectrum waveform, etc.) from at least one element in arrays 1710, 1720 and 1730. The transmitted ultrasound signal can travel through the test block and be received by the receiving hydrophone transducer elements 2091, 2092, 2093, 2094, 2095, 2096 and the transverse hydrophone 2086. It is important to note that detection of the ultrasonic signal or pulse as received by the hydrophone arrays cannot be detected accurately enough by cross correlation with the signal impressed on the probe element because the probe element itself distorts the signal.

Two innovative techniques are used to obtain the needed accuracy in finding the relative time delays and hence the relative distances. The first technique is to use cross correlation between the signal received at one element of the hydrophone (for example 2091) and the signal received at another element of the same hydrophone (for example 2093). The correlation peak will yield the time difference and thus the distance difference.

The second technique is to interpolate between samples of the received waveforms to obtain better time resolution than simply the sampling interval. Perhaps the best way to accomplish both of these tasks is to take the Fourier transform of both signals, fill in zeros for the high frequency components of a much larger transform. Call these larger transforms FFT1 and FFT2. Then find the peak of the inverse transform of (FFT1*(conjugate of FFT2)).

Figure 21A:
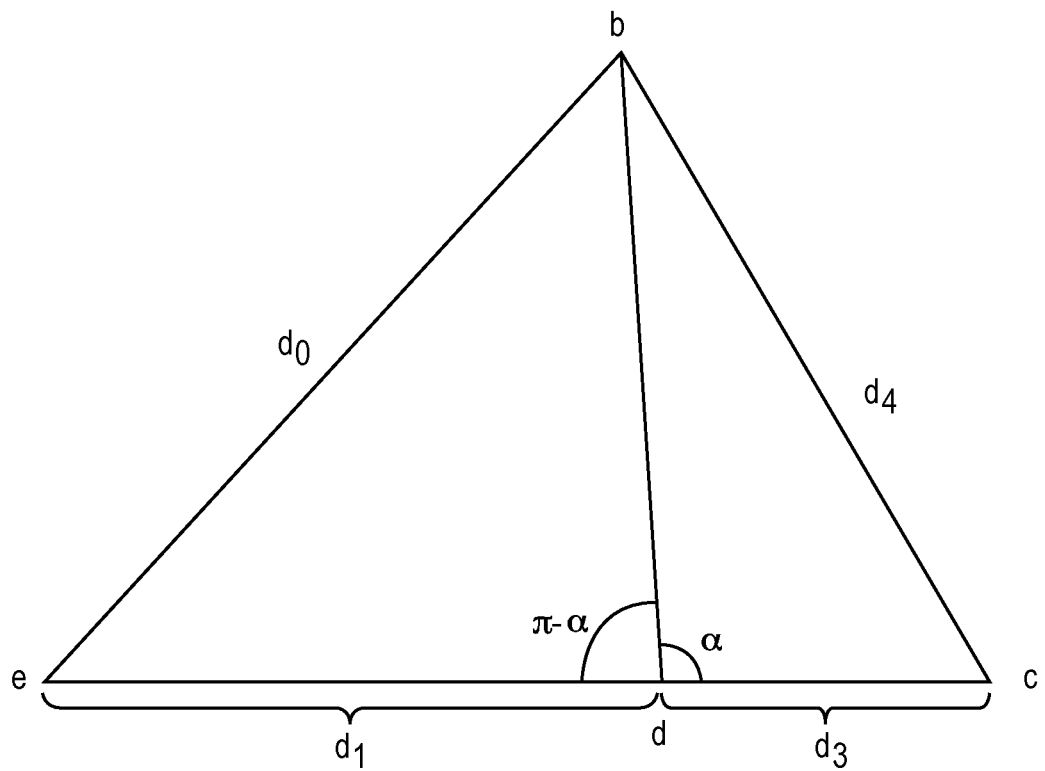
FIG. 21a is a graphic of basic geometry used to begin the conversion of distance difference into total distance.

A third technique is necessary to convert differential distances to total distance. Consider the triangle bce in FIG. 21a where the point b represents one of the elements for which we need to compute a position, and c and e are known reference points in the bottom of the water tank. It is desired to measure the lengths $d_4$ and $d_0$ by triangulation, but just knowing the difference between $d_0$ and $d_4$ is not enough. By adding a transverse hydrophone (see 2086 In FIG. 19a) in the bottom of the tank we have two triangles from which we can compute $d_0$ and $d_4$. Let e, d, and c be the locations of the hydrophones 2094, 2095 and 2096 or 2091, 2092 and 2093 of FIG. 19a.

For the following analysis, the hydrophones 2094, 2095 and 2096 must be on the same line and on a parallel line to that formed by 2091, 2092 and 2093. The distance between 2094 and 2095 is designated $d_1$, and the distance between 2095 and 2096 is designated $d_3$. $d_1$ and $d_3$ must be known precisely as this becomes the reference "yardstick" for the other measurements. 2095 should be roughly centered between 2094 and 2096LN, but $d_1$ does not need to equal $d_3$. The same requirements apply to R0, RC, and RN.

Let d2 be the reference distance and define measured distances as:

$$d_{2m}=d_2-d_2=0$$

$$d_{0m}=d_0-d_2$$

$$d_{4m}=d_4-d_2$$

From the law of cosines we have $$d_4^2=d_2^2+d_3^2-2d_3d_2\cos\alpha$$

$$d_0^2=d_2^2+d_1^2-2d_1d_2\cos(\pi-\alpha)=d_2^2+d_1^2+2d_1d_2\cos\alpha$$

$$\cos\alpha=(d_4^2-d_2^2-d_3^2)/(-2d_3d_2)=(d_0^2-d_2^2-d_1^2)/(2d_1d_2)$$

$$d_4^2-d_2^2-d_3^2=-(d_0^2-d_2^2-d_1^2)d_3/d_1$$

$$(d_{4m}+d_2)^2-d_2^2-d_3^2+(d_{0m}+d_2)^2d_3/d_1-d_2^2d_3/d_1-d_1d_3=0$$

Combining and cancelling terms this becomes $$d_2=(-d_{4m}^2+d_3^2-d_{0m}^2d_3/d_1+d_1d_3)/(2d_{4m}+2d_{0m}d_3/d_1)$$

Then $d_0=d_{0m}+d_2$ and $d_4=d_{4m}+d_2$

Thus we have the full measurements from received differential times.

Figure 23A:
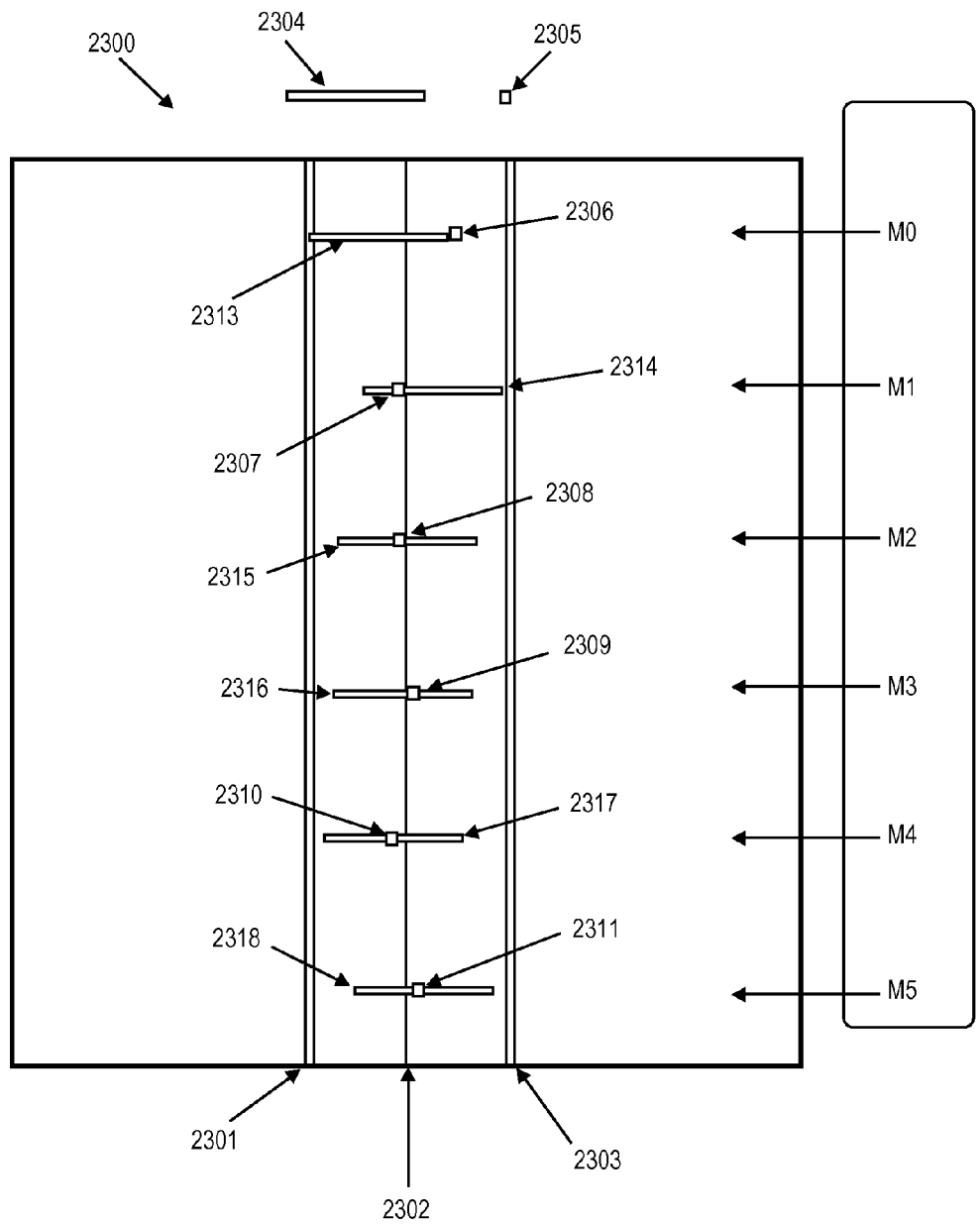
FIG. 23a is a representation of the graphical user interface or GUI developed to allow for the precise location of elements of multiple arrays under test.
Figure 23B:
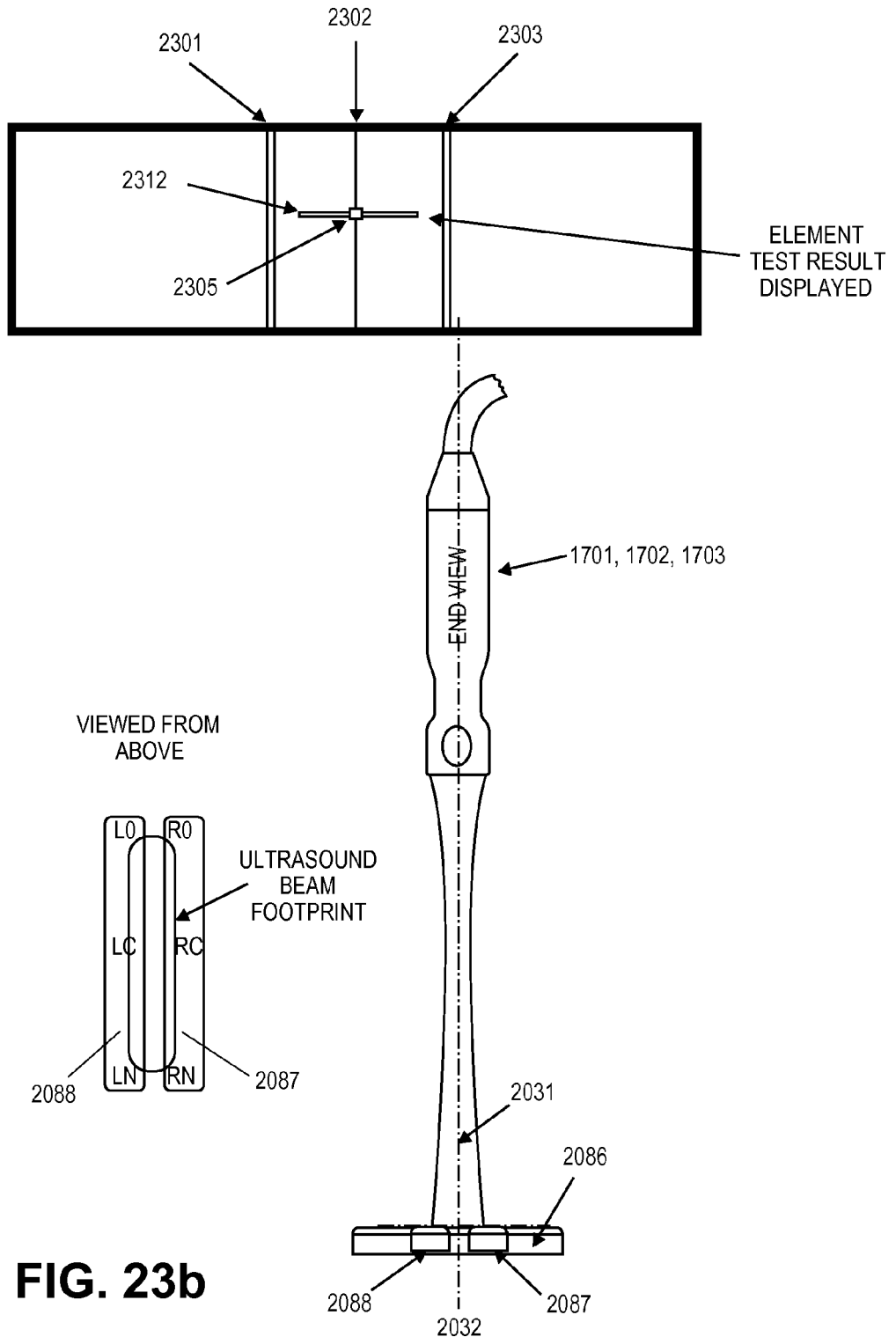
FIG. 23b depicts an array of elements under test with the ultrasound beam in the center of the transverse hydrophone, centered between the left and right hydrophones with the results displayed on the graphical user interface.

Two parallel "yardsticks" or right and left hydrophones are provided in the bottom of the tank in order to measure position along the z axis from FIG. 1, and as is illustrated in FIG. 23b. It will be the goal to position all of the probe elements from all three arrays 1701, 1702 and 1703 in a line midway between the two yardsticks using the various controls illustrated in FIG. 18b.

Figure 21B:
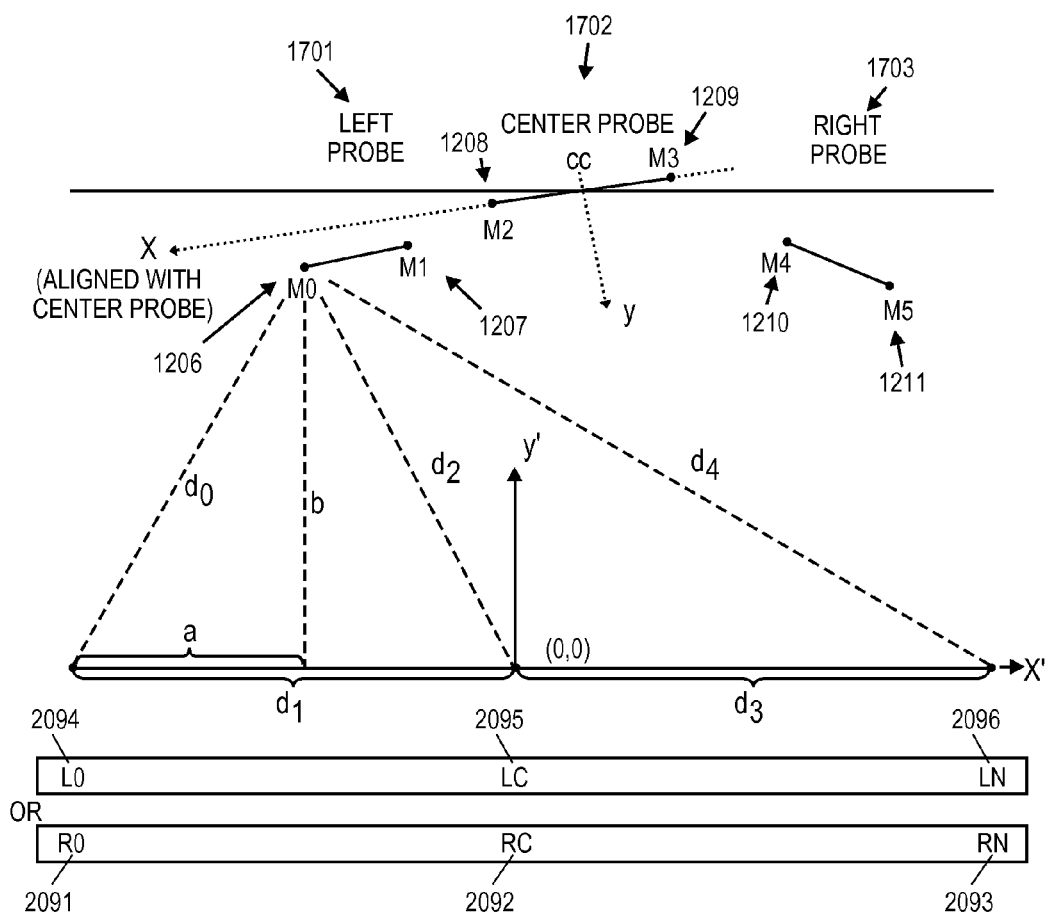
FIG. 21b is a graphic of the detailed geometry used to begin the conversion of distance difference into total distance allowing for the precision location of array element using three hydrophones.

Referring now to FIG. 21b, consider the measurement of the position of any probe element such as M0 1206. First, consider using the right yardstick R0-RC-RN 2091, 2092, 2093. By transmitting a chirp signal from element M0 1206 and receiving it on hydrophones at R0, RC, and RN 2091, 2092 and 2093, one can calculate the differential times for transmission along the paths $d_0$, $d_2$, and $d_4$. Times can be converted to distances if the speed of ultrasound of the test block medium is known. If the test block medium is water, the speed of sound is approximately sos=1.40238742+5.03821344*TE/1000.−5.80539349*TEA2/100000.+3.32000870*TE^3/10000000.−1.44537900*TE^4/1000000000.+2.99402365*TE^5/1000000000000. (mm per microsecond) where TE is the temperature in degrees Celsius. Differential distances can be converted to total distances according to the derivation above.

Now from trigonometry, distance $a=((d_0^2-d_4^2+(d_1+d_3)^2)/(2(d_1+d_3))$

The position along the x' axis is $d_1-a$.

Assuming that the element is midway between the two yardsticks, then the position along the y' axis is $\sqrt{(d_0^2-a^2-(zr/2)^2)}$.

Initially considerable error may occur as a result of this assumption, but the measurement of z will allow for adjustment of the element or the entire probe assembly until this assumption is satisfied.

Again referring to FIG. 21b, the same computations for x' and y' can be made using the left yardstick 2094, 2095 and 2095; and, the results can be averaged for increased accuracy. But the main reason for having two yardsticks is the ability to measure the z axis; the elements position in or out of the scan plane as illustrated in FIG. 1. Then the array alignment apparatus can display it (see FIG. 23a, 2300), and thus allow either manual (FIG. 18b) or automatic (FIG. 24) correction and alignment. The z variable is proportional to the time of arrival difference of the pulse as received at RC 2092 and LC 2095. The probe position should be adjusted until the time difference is close to zero. When this is done, all of the x and y measurements will be accurate and the relative positions of all of the elements will be known.

Finally a controller (such as a computer) can scan and find the maximum signal strength on the transverse hydrophone 2086 and record the angular displacement for the probe element.

To use the multiple aperture array alignment apparatus as a daily calibrator, multiple aperture ultrasound transducers will already be fully assembled, such as the embodiment illustrated in FIG. 22. Therefore, all of these measurements will have to be referenced to axes on the probe assembly. In the multi-aperture transducer probe assembly 2200 shown in FIG. 22, it would be reasonable to rotate and translate all measurements to a new coordinate system (x,y) centered on the center array. The appropriate coordinate system would be dependent on the ultrasound imaging system for which the probe assembly would be used. The multi-aperture probe can have a resident calibration memory or cal chip 2201 that can be programmed with calibration data received from the automated precision stage assembly, described below.

The transmit synchronization module 2202 is not related to calibration, but is necessary to identify the start of pulse when the probe is used as an add-on device with a host machine transmitting. The probe displacement sensor 2203 can be an accelerometer or gyroscope that senses the three-dimensional movement of the probe. During calibration, the probe must be securely attached to the array alignment apparatus so that the probe is still.

Referring now to FIG. 23a, a proprietary graphical user interface or GUI 2300, allows the elemental array data to be visualized in real-time allowing for correction of the x, y and z variation errors. The two wide vertical lines 2001 and 2003 represent the z positions of the yardsticks R0-RC-RN (2091, 2092, and 2093 from FIG. 19a) and L0-LC-LN (2094, 2095, and 2096 from FIG. 19a). The thinner vertical line 2302 is the z=0 line and the desired position of each of the elements of a probe system. The vertical position is the x coordinate.

Each small square, such as 2305, 2306, 2307, 2308, 2309, 2310 and 2011, is the position of a probe element in the x-z plane. In this example there are six small squares indicating the positions of the end elements of three probe heads. However, the positions of more or fewer elements could be displayed in this way. The thin horizontal lines 2312, 2313, 2314, 2315, 2316, 2317 and 2018 represent the directivity and angular spread of each element as detected on the multi-axis hydrophone. A useful angular spread measure is the number of hydrophone elements on the transverse hydrophone array which record signal strength greater or equal to half of the maximum strength.

Figure 23C:
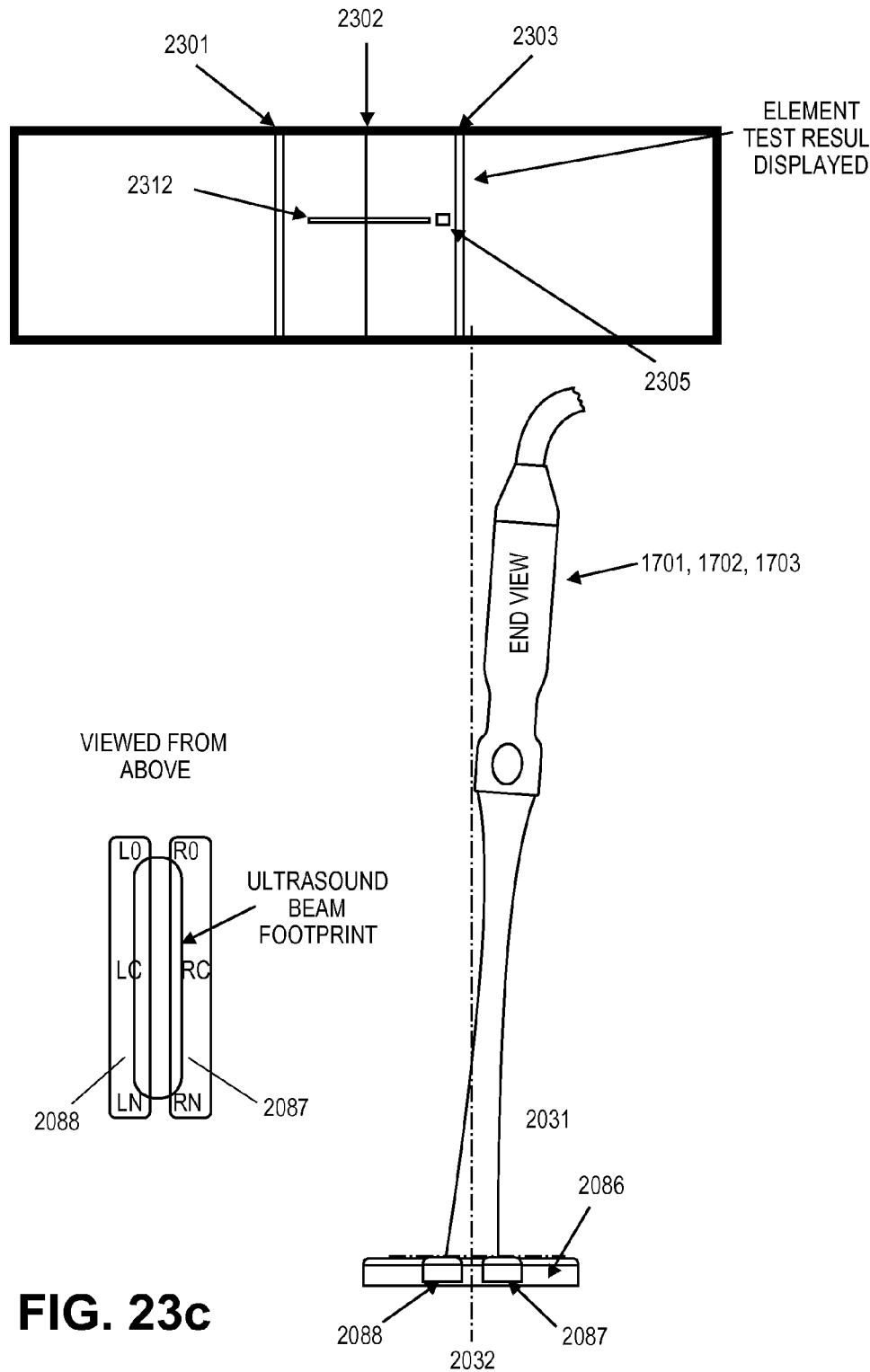
FIG. 23c is a representation of an array under test where its beam is on center but with the array to the right of center with the results displayed on the graphical user interface.

FIG. 23b depicts a probe element positioned correctly with the z position 2305 at or near z=0 and its directivity positioned over the centerline. In contrast, FIG. 23c depicts a probe element with its z position 2305 offset toward the right hydrophone. The resulting display shows the small square, 2305, to the right of centerline, 2302. Note that in this case, the element position is in error, but the element directivity remains over the centerline as indicated on the display by the horizontal line 2312 remaining centered over centerline, 2302.

Figure 23D:
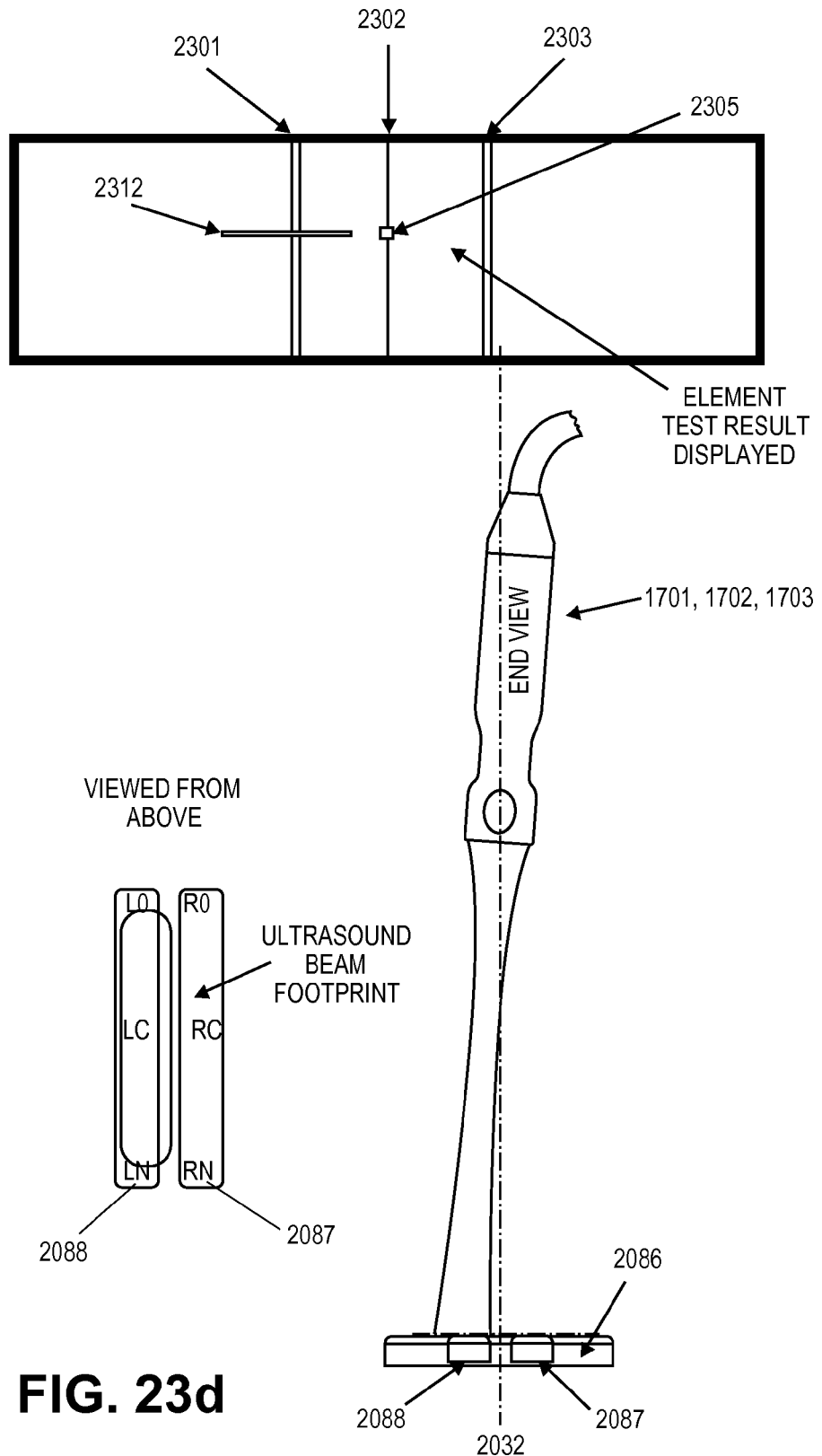
FIG. 23d is a representation of an array under test that is physically on the center axis, but has its beam is to the left of center with the results displayed on the graphical user interface.

Finally, FIG. 23d depicts a probe element correctly positioned with its z 2305 position at or near z=0, 2302. The directivity 2312, however, is misaligned in this case with an offset toward the left hydrophone as indicated by the horizontal line shifted to the left of centerline, 2302. In this case, the directivity needs to be corrected by adjusting the angulation to bring the directivity back over center. This could be accomplished, for example, by using controls 1805 and 1807 in FIG. 18b. Thus with this display, element position and directivity can be monitored simultaneously and both brought into alignment.

Adjustments of the probe position and angulation with the precision alignment stage assembly or assemblies should continue until all of the small squares and all of the horizontal lines are aligned on the center vertical line as closely as practicable, ensuring in alignment in the z axis. As this is done, the x and y positions will be computed accurately and no separate iteration will be required for these.

Figure 24:
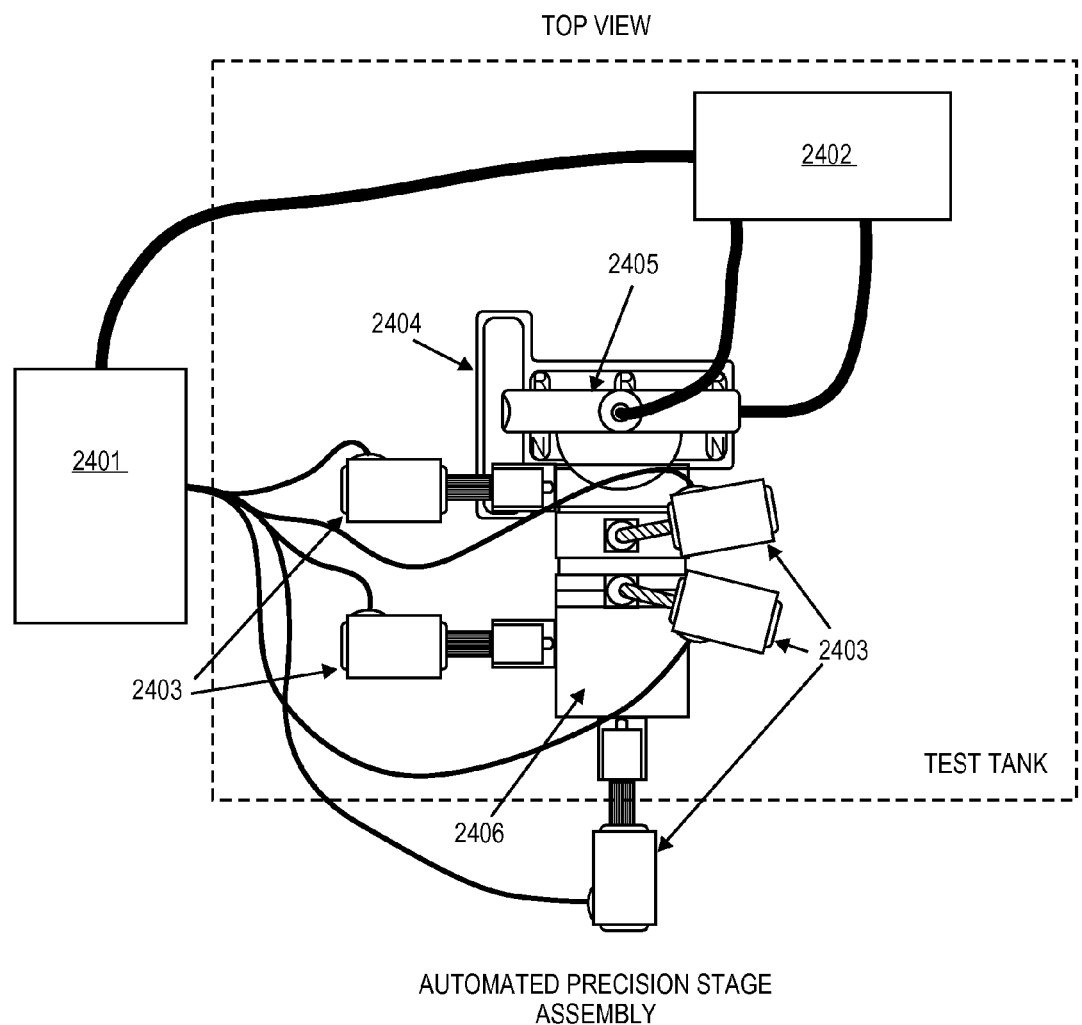
FIG. 24 is a representation of the automatic precision stage assembly and its major components.

In some manufacturing formats, arrays 2406 could be loaded into an automated precision stage assembly like the one in FIG. 24. Here, arrays while still within their nose pieces can still be manipulated. In FIG. 24, we see an automated precision stage assembly, 2406, fitted with precision stepper motors, 2403. Stepper motor controller, 2401, drives the transducer, 2405, under test in response to instructions from controller, 2402. The controller, 2401, evaluates data from the hydrophone assembly, 2404, and calculates transducer corrections. Test programs residing in the controller, 2402, provide transducer specific calibration data back to the transducer, 2405, under test incorporation in it's on board calibration chip, 2201. This automatically acquired element and array position data would be MAUI probe specific and would be used to optimize probe and system performance.

Figure 26A:
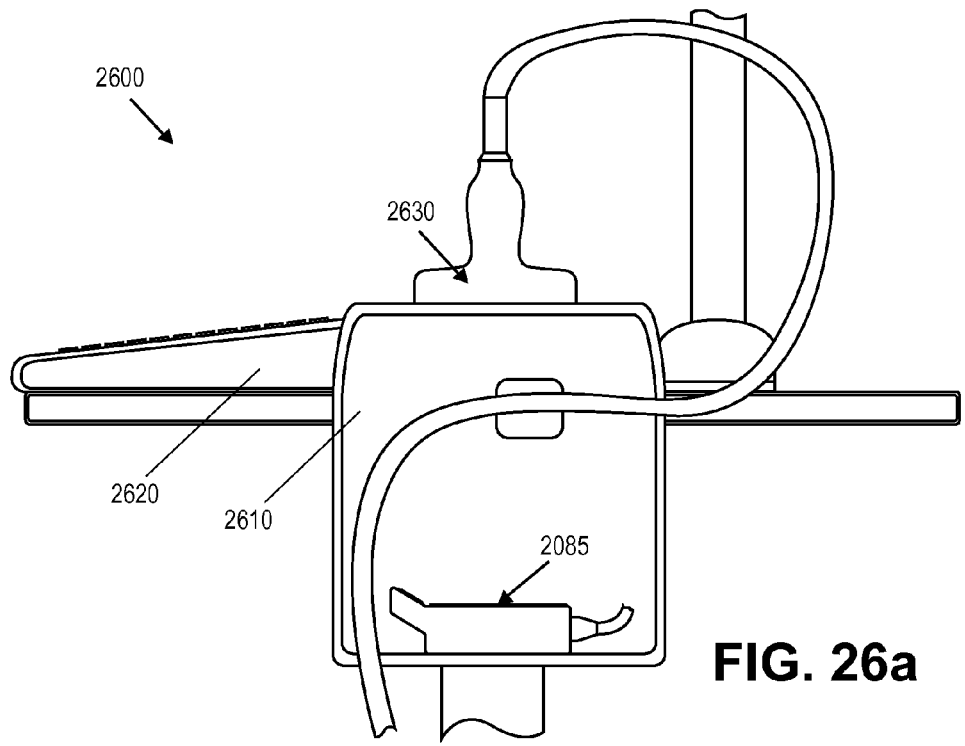
FIG. 26a is an illustration of an Onboard Calibration and Quality Assurance fixture mounted to the side of the MAUI standalone system. This illustration depicts a MAUI Radiology probe being evaluated.
Figure 26B:
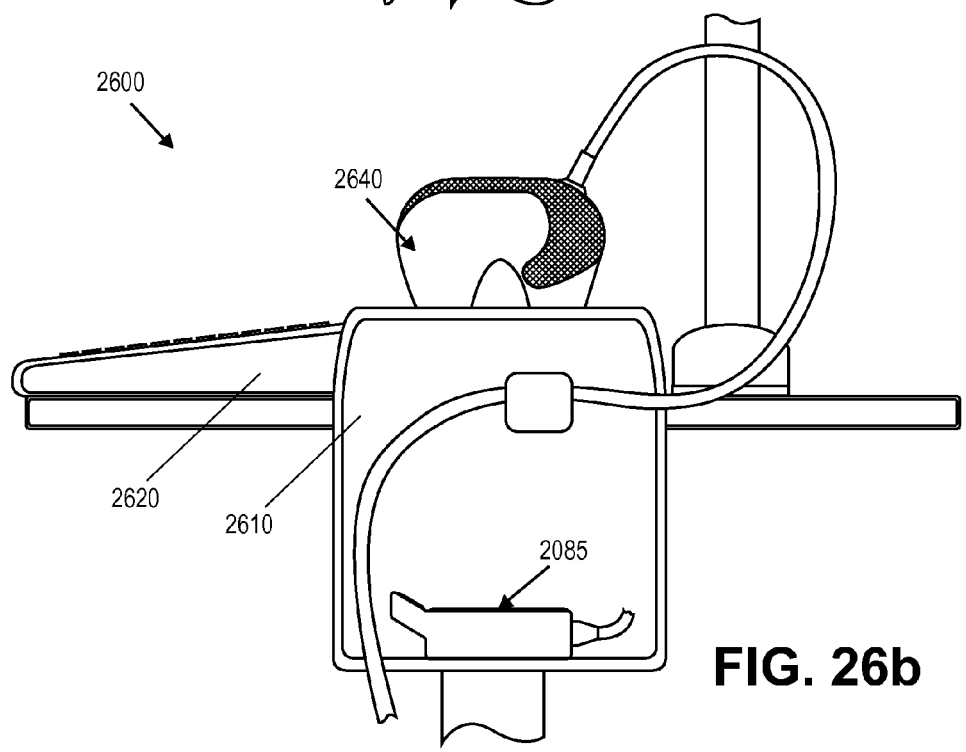
FIG. 26b illustrates the Onboard Calibration and Quality Assurance fixture evaluating a MAUI Cardiac probe.

Using the precision stage assemblies with the array alignment system is only part of the value of the system. FIGS. 26a and 26b illustrate array alignment systems 2610 attached to the control unit 2620 of an ultrasound machine 2600. A cut away shows hydrophone assembly 2085 is located at the bottom of the fluid filled system 2610. In FIG. 26a a MAUI general radiology probe 2630 is affixed to the system for testing. In FIG. 26b, a MAUI cardiac probe 2640 is affixed to the system for calibration. The portability of this system, therefore allows for calibration of probes in the field multiple times per day. Additionally the MAUI system would alert the operator if service or maintenance was required.

To calibrate a probe, MAUI electronic apparatus can send a test pattern to the arrays in the probe to transmit to the hydrophone assembly 2085. When the positions of the probes and their directivities are reported as a result of the sequence, the positions of all of the elements can be downloaded to a file specific to that probe. Each file is stored in the probe calibration chip 2201. The calibration chip reports element positions in x, y and z axes to every MAUI electronic apparatus it connects to, and therefore can perform multiple aperture imaging without recalibrating before use with a different MAUI apparatus. The calibration chip memory can also be used to analyze probe performance and reliability.

In the special case in which all of the transmit and receive elements are aligned in the same plane or are manufactured so that there is no adjustment in z position, a simplified alignment fixture can be used. Instead of two parallel "yardsticks" of hydrophones, a single yardstick can be used. In this case the probe would be centered over the single yardstick using a plumb bob or a clamping device. The x and y measurements would then be made assuming z=0 and zr=0. This is possible since accuracy in the value of z is much less critical in beamforming than is accuracy in the values of x and y. Thus adjusting z by the relatively crude methods of sighting with a plumb bob or clamping to a machined edge of the probe can be acceptable in spite of the high accuracy demands for measurement of x and y. Obviously, the cost of this simplified fixture would be much reduced resulting in a fixture which could be used in the field rather just in the probe assembly factory.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A method of aligning and assembling an ultrasound probe, the method comprising:
   placing a first transducer array within a first array carrier secured adjacent to a test block containing an ultrasound transmission medium;
   transmitting an ultrasound signal from the first transducer array into the ultrasound transmission medium;
   receiving the ultrasound signal with an ultrasonic sensor;
   determining a corrected alignment of the first transducer array based on the received signal;
   adjusting a position and/or an angulation of the first transducer array relative to the first array carrier with adjustment features of the first array carrier based on the corrected alignment;
   after adjusting the position and/or angulation of the first transducer array relative to the first array carrier, stabilizing the first transducer array in the first array carrier by inserting an acoustic damping material into a space between the first transducer array and the first array carrier, and curing the acoustic damping material.

2. The method of claim 1, further comprising, repeating the transmitting, receiving and adjusting steps at least once prior to the step of inserting the acoustic damping material.

3. The method of claim 1, further comprising inserting the first array carrier into a first transducer receptacle within a multiple aperture probe assembly.

4. The method of claim 1, further comprising:
   placing a second transducer array within a second array carrier;
   transmitting a second ultrasound signal from the second transducer array;
   receiving the second ultrasound signal with the ultrasonic sensor;
   determining a corrected alignment of the second transducer array based on the received signal;
   adjusting a position and/or an angulation of the second transducer array with adjustment features of the second array carrier to match the corrected alignment;
   after adjusting the position and/or angulation of the second transducer array relative to the second array carrier, stabilizing the second transducer array in the second array carrier by inserting a second acoustic damping material into a space between the second transducer array and the second array carrier, and curing the second acoustic damping material; and
   locking the first array carrier with the first array stabilized therein and the second array carrier with the second transducer array stabilized therein into respective precision transducer receptacles in a probe structural support member.

5. The method of claim 1, wherein the transmitting step comprises transmitting a test pattern signal from transducer elements of the transducer array into the test block.

6. The method of claim 5, wherein the receiving step further comprises receiving the test pattern signal with the ultrasonic sensor positioned at an opposite side of the test block from the transducer array, and wherein the determining step further comprises determining the corrected alignment of the transducer array by evaluating the received test pattern signal with a controller.

7. The method of claim 5, wherein the determining step further comprises comparing relative elapsed times between transmitting the test pattern signal and receiving the test pattern signal.

8. The method of claim 5, wherein the test block comprises a tank filled with a medium having a known speed of sound.

9. The method of claim 5, wherein the test block comprises a plurality of reflectors at fixed known locations within a medium having a known speed of sound.

10. The method of claim 9, wherein the transmitting and receiving steps are performed using the transducer array.

11. The method of claim 10, wherein determining a corrected alignment is based on displayed positions of the reflectors.

12. The method of claim 1, wherein the adjusting step further comprises automatically adjusting the position and/or angulation of the transducer array with adjustment features of the first array carrier.

13. The method of claim 1, wherein the adjusting step further comprises adjusting with a stepper motor the position and/or angulation of the transducer array with adjustment features of the first array carrier.

14. The method of claim 1, wherein the adjusting step further comprises turning a set screw in the first array carrier to adjust the position and/or angulation of the transducer array within the first array carrier.

* * * * *